US007198650B2

(12) United States Patent
Pourille-Grethen et al.

(10) Patent No.: US 7,198,650 B2
(45) Date of Patent: Apr. 3, 2007

(54) METHOD OF DYEING HUMAN KERATIN MATERIALS WITH A LIGHTENING EFFECT WITH COMPOSITIONS COMPRISING AT LEAST ONE FLUORESCENT DYE AND AT LEAST ONE AMPHOTERIC OR NONIONIC SURFACTANT, COMPOSITION THEREOF, PROCESS THEREOF, AND DEVICE THEREFOR

(75) Inventors: Chrystel Pourille-Grethen, Clichy (FR); Grégory Plos, Paris (FR)

(73) Assignee: L'Oreal S.A., Paris (FR)

( * ) Notice: Subject to any disclaimer, the term of this patent is extended or adjusted under 35 U.S.C. 154(b) by 20 days.

(21) Appl. No.: 10/814,338

(22) Filed: Apr. 1, 2004

(65) Prior Publication Data
US 2005/0005371 A1  Jan. 13, 2005

Related U.S. Application Data

(60) Provisional application No. 60/468,106, filed on May 6, 2003.

(30) Foreign Application Priority Data
Apr. 1, 2003 (FR) .................................. 03 04034

(51) Int. Cl.
*A61K 8/00* (2006.01)
(52) U.S. Cl. ...................... 8/405; 8/406; 8/407; 8/410; 8/411; 8/421; 8/648; 132/202; 132/208
(58) Field of Classification Search ................ 8/405, 8/406, 407, 410, 411, 421, 648; 132/202, 132/208
See application file for complete search history.

(56) References Cited

U.S. PATENT DOCUMENTS

| 2,261,002 A | 10/1941 | Ritter |
| 2,271,378 A | 1/1942 | Searle |
| 2,273,780 A | 2/1942 | Ditmar |
| 2,375,853 A | 5/1945 | Kirby et al. |
| 2,388,614 A | 11/1945 | Kirby et al. |
| 2,454,547 A | 11/1948 | Bock et al. |
| 2,798,053 A | 7/1957 | Brown |
| 2,851,424 A | 9/1958 | Switzer et al. |
| 2,923,692 A | 2/1960 | Ackerman et al. |
| 2,961,347 A | 11/1960 | Floyd |
| 2,979,465 A | 4/1961 | Parran et al. |
| 3,014,041 A | 12/1961 | Hausermann et al. |
| 3,206,462 A | 9/1965 | McCarty |
| 3,227,615 A | 1/1966 | Korden |
| 3,472,840 A | 10/1969 | Stone et al. |
| 3,632,559 A | 1/1972 | Matter et al. |
| 3,639,127 A | 2/1972 | Brooker et al. |
| 3,658,985 A | 4/1972 | Olson, Jr. et al. |
| 3,856,550 A | 12/1974 | Bens et al. |
| 3,874,870 A | 4/1975 | Green et al. |
| 3,910,862 A | 10/1975 | Barabas et al. |
| 3,912,808 A | 10/1975 | Soko |
| 3,915,921 A | 10/1975 | Schlatzer, Jr. |
| 3,917,817 A | 11/1975 | Vanlerberghe et al. |
| 3,929,990 A | 12/1975 | Green et al. |
| 3,966,904 A | 6/1976 | Green et al. |
| 3,986,825 A | 10/1976 | Sokol |
| 4,001,432 A | 1/1977 | Green et al. |
| 4,005,193 A | 1/1977 | Green et al. |
| 4,013,787 A | 3/1977 | Varlerberghe et al. |
| 4,025,617 A | 5/1977 | Green et al. |
| 4,025,627 A | 5/1977 | Green et al. |
| 4,025,653 A | 5/1977 | Green et al. |
| 4,026,945 A | 5/1977 | Green et al. |
| 4,027,020 A | 5/1977 | Green et al. |
| 4,031,307 A | 6/1977 | DeMartino et al. |
| 4,075,136 A | 2/1978 | Schaper |
| 4,131,576 A | 12/1978 | Iovine et al. |
| 4,157,388 A | 6/1979 | Christiansen |
| 4,165,367 A | 8/1979 | Chakrabarti |
| 4,166,894 A | 9/1979 | Schaper |
| 4,172,887 A | 10/1979 | Vanlerberghe et al. |

(Continued)

FOREIGN PATENT DOCUMENTS

AT        302 534        10/1972

(Continued)

OTHER PUBLICATIONS

English language Derwent Abstract of DE 199 23 438, Nov. 30, 2000.

(Continued)

*Primary Examiner*—Eisa Elhilo
(74) *Attorney, Agent, or Firm*—Finnegan, Henderson, Farabow, Garrett & Dunner L.L.P.

(57) ABSTRACT

The present disclosure relates to a method of dyeing human keratin materials with a lightening effect with a composition comprising, in a cosmetically acceptable medium, at least one fluorescent dye that is soluble in the cosmetically acceptable medium and at least one surfactant chosen from amphoteric surfactants and nonionic surfactants.

The present disclosure also relates to compositions comprising at least one particular fluorescent dye that is soluble in the cosmetically acceptable medium and at least one surfactant chosen from amphoteric surfactants and nonionic surfactants, and also to processes using these compositions, and devices for these compositions.

86 Claims, No Drawings

U.S. PATENT DOCUMENTS

| | | | |
|---|---|---|---|
| 4,185,087 A | 1/1980 | Morlino | |
| 4,189,468 A | 2/1980 | Vanlerberghe et al. | |
| 4,197,865 A | 4/1980 | Jacquet et al. | |
| 4,217,914 A | 8/1980 | Jacquet et al. | |
| 4,223,009 A | 9/1980 | Chakrabarti | |
| 4,237,243 A | 12/1980 | Quack et al. | |
| 4,240,450 A | 12/1980 | Grollier et al. | |
| 4,256,458 A | 3/1981 | Degen et al. | |
| 4,277,581 A | 7/1981 | Vanlerberghe et al. | |
| 4,381,919 A | 5/1983 | Jacquet et al. | |
| 4,422,853 A | 12/1983 | Jacquet et al. | |
| 4,445,521 A | 5/1984 | Grollier et al. | |
| 4,509,949 A | 4/1985 | Huang et al. | |
| 4,591,160 A | 5/1986 | Grollier | |
| 4,608,250 A | 8/1986 | Jacquet et al. | |
| 4,693,935 A | 9/1987 | Mazurek | |
| 4,702,906 A | 10/1987 | Jacquet et al. | |
| 4,719,099 A | 1/1988 | Grollier et al. | |
| 4,719,282 A | 1/1988 | Nadolsky et al. | |
| 4,728,571 A | 3/1988 | Clemens et al. | |
| 4,761,273 A | 8/1988 | Grollier et al. | |
| 4,781,724 A | 11/1988 | Wajaroff et al. | |
| 4,823,985 A | 4/1989 | Grollier et al. | |
| 4,839,166 A | 6/1989 | Grollier et al. | |
| 4,948,579 A | 8/1990 | Jacquet et al. | |
| 4,961,925 A | 10/1990 | Tsujino et al. | |
| 4,972,037 A | 11/1990 | Garbe et al. | |
| 4,996,059 A | 2/1991 | Grollier et al. | |
| 5,009,880 A | 4/1991 | Grollier et al. | |
| 5,089,252 A | 2/1992 | Grollier et al. | |
| 5,139,037 A | 8/1992 | Grollier et al. | |
| 5,188,639 A | 2/1993 | Schultz et al. | |
| 5,196,189 A | 3/1993 | Jacquet et al. | |
| 5,356,438 A | 10/1994 | Kim et al. | |
| 5,445,655 A | 8/1995 | Kuhn et al. | |
| 5,635,461 A | 6/1997 | Onitsuka et al. | |
| 5,708,151 A | 1/1998 | Möckli | |
| 5,744,127 A * | 4/1998 | Giuseppe et al. | 424/59 |
| 5,792,221 A | 8/1998 | Lagrange et al. | |
| 5,830,446 A | 11/1998 | Berthiaume et al. | |
| 5,833,997 A | 11/1998 | Mahieu et al. | |
| 5,873,494 A | 2/1999 | Dallas, Jr. | |
| 5,958,392 A | 9/1999 | Grollier et al. | |
| 5,962,522 A | 10/1999 | Wacher et al. | |
| 6,106,577 A | 8/2000 | Audousset et al. | |
| 6,120,780 A | 9/2000 | Dupuis et al. | |
| 6,156,077 A * | 12/2000 | Shibata et al. | 8/406 |
| 6,180,666 B1 | 1/2001 | Wacher et al. | |
| 6,260,556 B1 | 7/2001 | Legrand et al. | |
| 6,391,062 B1 | 5/2002 | Vandenbossche et al. | |
| 6,436,151 B2 | 8/2002 | Cottard et al. | |
| 6,436,153 B2 * | 8/2002 | Rondeau | 8/426 |
| 6,475,248 B2 | 11/2002 | Ohashi et al. | |
| 6,592,630 B2 | 7/2003 | Matsunaga et al. | |
| 6,616,709 B2 | 9/2003 | Ohashi et al. | |
| 6,712,861 B2 | 3/2004 | Rondeau | |
| 2001/0010812 A1 | 8/2001 | Chevalier et al. | |
| 2001/0023514 A1* | 9/2001 | Cottard et al. | 8/406 |
| 2001/0023515 A1 | 9/2001 | Cottard et al. | |
| 2001/0031270 A1 | 10/2001 | Douin et al. | |
| 2001/0054206 A1* | 12/2001 | Matsunaga et al. | 8/405 |
| 2001/0055580 A1 | 12/2001 | Belli et al. | |
| 2002/0004956 A1 | 1/2002 | Rondeau | |
| 2002/0012681 A1 | 1/2002 | George et al. | |
| 2002/0026676 A1 | 3/2002 | Ohashi et al. | |
| 2002/0046431 A1 | 4/2002 | Laurent et al. | |
| 2002/0046432 A1 | 4/2002 | Rondeau | |
| 2002/0088063 A1 | 7/2002 | Ohashi et al. | |
| 2002/0131941 A1 | 9/2002 | Habeck et al. | |
| 2002/0176836 A9 | 11/2002 | Belli et al. | |
| 2002/0176875 A9 | 11/2002 | Douin et al. | |
| 2003/0000023 A9 | 1/2003 | Rondeau | |
| 2003/0019052 A1 | 1/2003 | Pratt | |
| 2003/0019053 A9 | 1/2003 | Rondeau | |
| 2003/0055268 A1 | 3/2003 | Pasquier et al. | |
| 2003/0074747 A1 | 4/2003 | Vuarier et al. | |
| 2003/0124079 A1 | 7/2003 | Mougin et al. | |
| 2003/0131424 A1 | 7/2003 | Audousset et al. | |
| 2004/0019981 A1 | 2/2004 | Cottard et al. | |
| 2004/0034945 A1 | 2/2004 | Javet et al. | |
| 2004/0037796 A1 | 2/2004 | Cottard et al. | |
| 2004/0049860 A1 | 3/2004 | Cottard et al. | |
| 2004/0141943 A1 | 7/2004 | Mougin et al. | |
| 2004/0148711 A1 | 8/2004 | Rondeau | |
| 2004/0205901 A1 | 10/2004 | Cottard et al. | |
| 2005/0005368 A1 | 1/2005 | Plos et al. | |
| 2005/0005369 A1 | 1/2005 | Plos et al. | |
| 2005/0028301 A1 | 2/2005 | Pastore | |
| 2005/0144741 A1 | 7/2005 | Lang et al. | |

FOREIGN PATENT DOCUMENTS

| | | |
|---|---|---|
| CA | 1255603 | 6/1989 |
| CH | 487 231 | 3/1970 |
| DE | 33 13 332 | 10/1984 |
| DE | 196 46 804 A1 | 5/1997 |
| DE | 199 23 438 | 11/2000 |
| DE | 199 26 377 A1 | 12/2000 |
| DE | 100 29 441 A1 | 1/2002 |
| DE | 101 41 683 A1 | 6/2003 |
| DE | 101 48 844 A1 | 10/2003 |
| EP | 0 087 060 B1 | 8/1983 |
| EP | 0 095 238 A2 | 11/1983 |
| EP | 0 080 976 B1 | 9/1986 |
| EP | 0 173 109 | 10/1989 |
| EP | 0 370 470 B1 | 5/1990 |
| EP | 0 412 704 B1 | 2/1991 |
| EP | 0 412 707 B1 | 2/1991 |
| EP | 0 445 342 B1 | 9/1991 |
| EP | 0 486 135 B1 | 5/1992 |
| EP | 0 122 324 B2 | 2/1993 |
| EP | 0 337 354 B1 | 2/1994 |
| EP | 0 582 152 B1 | 2/1994 |
| EP | 0 395 282 | 3/1995 |
| EP | 0 503 853 | 5/1996 |
| EP | 0 714 954 A2 | 6/1996 |
| EP | 0 733 355 A2 | 9/1996 |
| EP | 0 808 150 | 11/1997 |
| EP | 0 815 828 B1 | 6/1999 |
| EP | 0 970 684 A1 | 1/2000 |
| EP | 1 023 891 B1 | 8/2000 |
| EP | 1 099 437 | 5/2001 |
| EP | 1 132 076 A1 | 9/2001 |
| EP | 1 133 977 A2 | 9/2001 |
| EP | 1 191 041 A2 | 3/2002 |
| FR | 1492597 | 9/1966 |
| FR | 1583363 | 10/1969 |
| FR | 2077143 | 10/1971 |
| FR | 2080759 | 11/1971 |
| FR | 2103210 | 7/1972 |
| FR | 2162025 | 7/1973 |
| FR | 2190406 | 2/1974 |
| FR | 2252840 | 6/1975 |
| FR | 2270846 | 12/1975 |
| FR | 2280361 | 2/1976 |
| FR | 2316271 | 1/1977 |
| FR | 2320330 | 3/1977 |
| FR | 2336434 | 7/1977 |
| FR | 2368508 | 5/1978 |
| FR | 2589476 | 5/1978 |
| FR | 2383660 | 10/1978 |
| FR | 2393573 | 1/1979 |
| FR | 2411219 | 7/1979 |
| FR | 2416723 | 9/1979 |

| | | |
|---|---|---|
| FR | 2470596 | 6/1981 |
| FR | 2505348 | 11/1982 |
| FR | 2519863 | 7/1983 |
| FR | 2542997 | 9/1984 |
| FR | 2586913 | 3/1987 |
| FR | 2598611 | 11/1987 |
| FR | 2692572 | 6/1992 |
| FR | 2741261 | 5/1997 |
| FR | 2797877 | 3/2001 |
| FR | 2800612 | 5/2001 |
| FR | 2811993 | 1/2002 |
| FR | 2820032 | 8/2002 |
| FR | 2830189 | 4/2003 |
| GB | 746864 | 3/1956 |
| GB | 759385 | 10/1956 |
| GB | 1214394 | 1/1970 |
| GB | 1546809 | 5/1979 |
| GB | 1 554 331 | 10/1979 |
| JP | 48-17362 | 5/1973 |
| JP | 54-86521 | 7/1979 |
| JP | 2-200612 | 8/1990 |
| JP | 6-128128 | 5/1994 |
| JP | 6-183935 | 7/1994 |
| JP | 6-227954 | 8/1994 |
| JP | 8-183716 | 7/1996 |
| JP | 8-208448 | 8/1996 |
| JP | 8-259426 | 10/1996 |
| JP | 10-23629 | 9/1998 |
| JP | 11-021214 | 1/1999 |
| JP | 11-60453 | 3/1999 |
| JP | 11-343218 | 12/1999 |
| JP | 2000-01417 | 1/2000 |
| JP | 2000-86472 | 3/2000 |
| JP | 2000-505841 | 5/2000 |
| JP | 2001-172120 | 6/2001 |
| JP | 2001-220330 | 8/2001 |
| JP | 2001-226217 | 8/2001 |
| JP | 2001-261534 | 9/2001 |
| JP | 2001-261536 | 9/2001 |
| JP | 2001-294519 | 10/2001 |
| JP | 2001-516701 | 10/2001 |
| JP | 2001-516706 | 10/2001 |
| JP | 2001-516707 | 10/2001 |
| JP | 2002-12523 | 1/2002 |
| JP | 2002-12530 | 1/2002 |
| JP | 2002-47151 | 2/2002 |
| JP | 2002-226338 | 8/2002 |
| JP | 2002-249419 | 9/2002 |
| JP | 2003-55177 | 2/2003 |
| JP | 2004-059468 | 2/2004 |
| WO | WO 93/11103 | 6/1993 |
| WO | WO 93/23009 | 11/1993 |
| WO | WO 93/23446 | 11/1993 |
| WO | WO 94/02022 | 2/1994 |
| WO | WO 95/00578 | 1/1995 |
| WO | WO 95/01772 | 1/1995 |
| WO | WO 95/15144 | 6/1995 |
| WO | WO 97/18795 | 5/1997 |
| WO | WO 99/12846 | 3/1999 |
| WO | WO 99/13822 | 3/1999 |
| WO | WO 99/13823 | 3/1999 |
| WO | WO 99/13824 | 3/1999 |
| WO | WO 99/13828 | 3/1999 |
| WO | WO 99/13841 | 3/1999 |
| WO | WO 99/13845 | 3/1999 |
| WO | WO 99/13846 | 3/1999 |
| WO | WO 99/13847 | 3/1999 |
| WO | WO 99/13849 | 3/1999 |
| WO | WO 99/20235 A1 | 4/1999 |
| WO | WO 00/68282 | 11/2000 |
| WO | WO 00/71085 A2 | 11/2000 |
| WO | WO 01/43714 A1 | 6/2001 |
| WO | WO 01/62759 A1 | 8/2001 |
| WO | WO 01/78669 | 10/2001 |
| WO | WO 02/32386 A2 | 4/2002 |
| WO | WO 02/38115 A1 | 5/2002 |
| WO | WO 02/39964 A1 | 5/2002 |
| WO | WO 02/45673 A2 | 6/2002 |
| WO | WO 02/58646 A1 | 8/2002 |
| WO | WO 02/58647 A1 | 8/2002 |
| WO | WO 02/074270 | 9/2002 |
| WO | WO 03/22232 A2 | 3/2003 |
| WO | WO 03/28685 A1 | 4/2003 |
| WO | WO 03/029359 | 4/2003 |

OTHER PUBLICATIONS

D. Williams et al., "Chemistry and Technology of the Cosmetics and Toiletries Industry", ed. 2, pp. 77-78, 1996.
M. Schlossmann, "The Chemistry and Manufacture of Cosmetics: Formulating", vol. 2, ed. 3, pp. 522-526, 2000.
CAS Abstract for JP 2000-136340—Chemical Abstracts Service; Database Accession No. 2000: 317079; XP-002269220, JP 2000136340 (Pentel Co., Ltd.), May 16, 2000.
Co-pending U.S. Appl. No. 10/814,334, filed Apr. 1, 2004.
Co-pending U.S. Appl. No. 10/814,333, filed Apr. 1, 2004.
Co-pending U.S. Appl. No. 10/814,430, filed Apr. 1, 2004.
Co-pending U.S. Appl. No. 10/814,305, filed Apr. 1, 2004.
Co-pending U.S. Appl. No. 10/814,300, filed Apr. 1, 2004.
Co-pending U.S. Appl. No. 10/814,335, filed Apr. 1, 2004.
Co-pending U.S. Appl. No. 10/814,428, filed Apr. 1, 2004.
Co-pending U.S. Appl. No. 10/490,869, filed Apr. 1, 2004.
Co-pending U.S. Appl. No. 10/814,236, filed Apr. 1, 2004.
Co-pending U.S. Appl. No. 10/814,337, filed Apr. 1, 2004.
Co-pending U.S. Appl. No. 10/814,585, filed Apr. 1, 2004.
Co-pending U.S. Appl. No. 10/742,995, filed Dec. 23, 2003.
Co-pending U.S. Appl. No. 10/814,336, filed Apr. 1, 2004.
English Language Derwent Abstract of DE 100 29 441.
English Language Derwent Abstract of DE 101 41 683.
English Language Derwent Abstract of DE 101 48 844.
English Language Derwent Abstract of DE 199 26 377.
English Language Derwent Abstract of DE 33 133 32.
English Language Derwent Abstract of EP 0 080 976.
English Language Derwent Abstract of EP 0 087 060.
English Language Derwent Abstract of EP 0 808 150.
English Language Derwent Abstract of EP 1 023 891.
English Language Derwent Abstract of EP 1 099 437.
English Language Derwent Abstract of FR 2,773,864.
English Language Derwent Abstract of FR 2,797,877.
English Language Derwent Abstract of FR 2,800,612.
English Language Abstract of FR 2 598 476 (EP 0 225 261) from EPO website.
English Language Derwent Abstract of JP 10-23629.
English Language Derwent Abstract of JP 11-060453.
English Language Derwent Abstract of JP 11-21214.
English Language Derwent Abstract of JP 2000-1417.
English Language Derwent Abstract of JP 2000-086472.
English Language Derwent Abstract of JP 2001-172120.
English Language Derwent Abstract of JP 2001-261534.
English Language Derwent Abstract of JP 2001-294519.
English Language Derwent Abstract of JP 2001-516701.
English Language Derwent Abstract of JP 2001-516706.
English Language Derwent Abstract of JP 2001-516707.
English Language Derwent Abstract of JP 2002-226338.
English Language Abstract of 2002-47151 from Aurigin database.
English Language Abstract of JP 2002-249419 from Japio database.
English Language Derwent Abstract of JP 2004-59468.
English Language Derwent Abstract of JP 2-200612.
English Language Derwent Abstract of JP 6-183935.
English Language Derwent Abstract of JP 6-227954.
English Language Derwent Abstract of JP 8-183716.
English Language Derwent Abstract of JP 8-208448.
French Search Report for French Patent Application No. FR 03/04021, priority document for U.S. Appl. No. 10/814,337.

French Search Report for French Patent Application No. FR 03/04022, priority document for co-pending U.S. Appl. No. 10/814,336.

French Search Report for French Patent Application No. FR 03/04024, priority document for co-pending U.S. Appl. No. 10/814,585.

French Search Report for French Patent Application No. FR 03/04026, priority document for co-pending U.S. Appl. No. 10/814,335.

French Search Report for French Patent Application No. FR 03/04027, priority document for co-pending U.S. Appl. No. 10/814,428.

French Search Report for French Patent Application No. FR 03/04028, priority document for co-pending U.S. Appl. No. 10/814,236.

French Search Report for French Patent Application No. FR 03/04029, priority document for co-pending U.S. Appl. No. 10/814,430.

French Search Report for French Patent Application No. FR 03/04030, priority document for co-pending U.S. Appl. No. 10/814,300.

French Search Report for French Patent Application No. FR 03/04031, priority document for co-pending U.S. Appl. No. 10/814,333.

French Search Report for French Patent Application No. FR 03/04033, priority document for co-pending U.S. Appl. No. 10/814,334.

French Search Report for French Patent Application No. FR 03/04034, priority document for co-pending U.S. Appl. No. 10/814,338.

French Search Report for French Patent Application No. FR 03/04035, priority document for co-pending U.S. Appl. No. 10/814,305.

French Search Report for French Patent Application No. FR 02/16669, priority document for co-pending U.S. Appl. No. 10/742,995.

International Search Report for PCT Application No. PCT/FR 02/03252, (for co-pending U.S. Appl. No. 10/490,869), Jan. 20, 2003.

Office Action mailed Nov. 17, 2005 in co-pending U.S. Appl. No. 10/814,336.

Office Action mailed Mar. 15, 2006 in co-pending U.S. Appl. No. 10/814,305.

Office Action mailed Mar. 23, 2006 in co-pending U.S. Appl. No. 10/814,300.

Office Action mailed Nov. 3, 2005 in co-pending U.S. Appl. No. 10/490,869.

Office Action mailed Nov. 2, 2005 in co-pending U.S. Appl. No. 10/742,995.

Jacobi, Otto and Jacobi, Gertrud, "Investigation into the reciprocal action of cosmetics and the biosphere of the stratum corneuum of the skin," *Cosmetics and Toiletries*, 91:25-32 (Jan. 1976).

Science Des Traitements Capillaires [Hair Treatment Sciences] by Charles Zviak, 1988, published by Masson, pp. 215 and 278.

Yuuki Kagoubutsu Jilen (Dictionary of Organic Compounds), Kodansha Ltd., Aug. 10, 2002, p. 908.

G. Fonnum, J. Bakke and Fk. Hansen—Colloid Polym. Sci 271, 380-389 (1993).

Zviak, C., The Science of Hair Care, pp. 215 and 278 (1986).

\* cited by examiner

METHOD OF DYEING HUMAN KERATIN MATERIALS WITH A LIGHTENING EFFECT WITH COMPOSITIONS COMPRISING AT LEAST ONE FLUORESCENT DYE AND AT LEAST ONE AMPHOTERIC OR NONIONIC SURFACTANT, COMPOSITION THEREOF, PROCESS THEREOF, AND DEVICE THEREFOR

This application claims benefit of U.S. Provisional Application No. 60/468,106, filed May 6, 2003.

The present disclosure relates to methods for dyeing with a lightening effect, human keratin materials, for example keratin fibers, and further for example artificially dyed or pigmented hair and dark skin, with a composition comprising at least one fluorescent dye and at least one surfactant chosen from amphoteric and nonionic surfactants. The present disclosure also relates to these novel compositions, to processes for using these compositions, and to devices for these compositions.

It is common for individuals with dark skin to wish to lighten their skin and for this purpose to use cosmetic or dermatological compositions comprising bleaching agents.

The substances most commonly used as bleaching agents are hydroquinone and its derivatives, kojic acid and its derivatives, azelaic acid, arbutin and its derivatives, alone or in combination with other active agents.

However, these agents are not without their drawbacks. For example, they need to be used for a long time and in large amounts in order to obtain a bleaching effect on the skin. No immediate effect can be observed on applying compositions comprising them.

In addition, hydroquinone and its derivatives may be used in an amount that is effective to produce a visible bleaching effect. For example, hydroquinone is known for its cytotoxicity towards melanocyte.

Moreover, kojic acid and its derivatives have the drawback of being expensive and consequently of not being able to be used in large amounts in products for commercial mass distribution.

There is thus still a need in the art for cosmetic compositions that allow a lighter, uniform, homogeneous skin tone of natural appearance to be obtained, wherein these compositions may also have satisfactory transparency after application to the skin.

In the field of haircare, mention may be made of two major types of hair dyeing.

The first is semi-permanent dyeing or direct dyeing, which uses dyes capable of giving the hair's natural color a more or less pronounced modification that can withstand shampooing several times. These dyes may also be referred to as direct dyes and may be used in two different ways. The colorations may be performed by applying the composition comprising the at least one direct dye directly to the keratin fibers, or by applying a mixture, prepared extemporaneously, of a composition comprising the at least one direct dye with a composition comprising an oxidizing bleaching agent, for example an aqueous hydrogen peroxide solution. Such a process may be referred to as "lightening direct dyeing".

The second major type of hair dyeing is permanent dyeing or oxidation dyeing. This may be performed with "oxidation" dye precursors, which are colorless or weakly colored compounds which, once mixed with oxidizing products, at the time of use, can give rise to colored compounds and dyes via a process of oxidative condensation. It is often necessary to combine at least one direct dye with the oxidation bases and couplers in order to neutralize or attenuate the shades with too much of a red, orange or golden glint or, alternatively, to accentuate these red, orange or golden glints.

Among the available direct dyes, nitrobenzene direct dyes are not sufficiently strong, and indoamines, quinone dyes and natural dyes have low affinity for keratin fibers and consequently may lead to colorations that are not sufficiently fast with respect to the various treatments to which the fibers may be subjected, such as shampooing.

In addition, there is a need in the art to obtain a lightening effect on human keratin fibers. This lightening may be obtained via a process of bleaching the melanins of the hair via an oxidizing system generally comprising hydrogen peroxide optionally combined with persalts. This bleaching system has the drawback of degrading the keratin fibers and of impairing their cosmetic properties.

One aspect of the present disclosure thus relates to compositions that can provide solutions to at least one of the drawbacks of the prior art. In one aspect, the present disclosure proposes compositions with at least one of: good dyeing affinity for keratin fibers, good resistance properties with respect to external agents, such as shampoos, and compositions that also may make it possible to obtain lightening without impairing the fiber.

The present inventors have found that the use of fluorescent dyes, such as those in the orange range, when put in the presence of particular surfactants, may avoid one ore more of the drawbacks found in the prior art.

Thus, disclosed herein is a method for dyeing with a lightening effect, human keratin materials, by applying to the keratin materials a composition comprising, in a cosmetically acceptable medium, at least one fluorescent dye that is soluble in the medium; and at least one surfactant chosen from amphoteric surfactants chosen from betaines and imidazolium derivatives, and from nonionic surfactants chosen from alkylpyrrolidones, oxyalkylenated fatty alcohol ethers, glycerolated fatty alcohol ethers, fatty acid esters of oxyalkylenated monoalcohols, fatty acid esters of glycerolated monoalcohols, fatty acid esters of optionally oxyalkylenated polyols, and fatty acid esters of optionally glycerolated polyols.

Also disclosed herein is a composition comprising, in a cosmetically acceptable medium, at least one fluorescent dye that is soluble in the medium, wherein the at least one fluorescent dye does not comprise three fused rings, wherein one of said rings is a monocationic heterocyle comprising two nitrogen atoms; and wherein the at least one fluorescent dye is not 2-[2-(4-dialkylamino)phenylethenyl]-1-alkylpyridinium, wherein the alkyl radical of the pyridinium nucleus is chosen from methyl and ethyl radicals, and that of the benzene nucleus is chosen from methyl radicals, and wherein the counterion is a halide; and at least one surfactant chosen from amphoteric surfactants chosen from betaines and imidazolium derivatives, and from nonionic surfactants chosen from alkylpyrrolidones, oxyalkylenated fatty alcohol ethers, glycerolated fatty alcohol ethers, fatty acid esters of oxyalkylenated monoalcohols, fatty acid esters of glycerolated monoalcohols, fatty acid esters of optionally oxyalkylenated polyols, and fatty acid esters of optionally glycerolated polyols.

Another subject of the present disclosure concerns a process for dyeing keratin fibers, such as hair, with a lightening effect, comprising:
  a) applying to the keratin fibers, for a time that is sufficient to develop the desired coloration and lightening, a composition according to the present disclosure,
  b) optionally rinsing the keratin fibers, c) optionally washing the keratin fibers with shampoo and rinsing the keratin fibers, and
d) drying the keratin fibers or leaving the keratin fibers to dry.

Also disclosed herein is a process for dyeing skin, for example dark skin, with a lightening effect, comprising applying the composition according to the present disclosure to the skin, then drying the skin or leaving it to dry.

The compositions used according to the present disclosure may also allow better diffusion of the fluorescent dye into the keratin materials, which may be reflected by an increased fluorescent effect, by a lightening effect that is greater and thus also by a lightness that is greater than that obtained with the fluorescent dye used alone.

Better resistance of the result with respect to washing or shampooing may also be found.

Other characteristics and advantages of the present disclosure will emerge more clearly on reading the description and the examples that follow.

Unless otherwise indicated, the limits of the ranges of values that are given in the description are included in these ranges.

As mentioned previously, a subject of the present disclosure is a method for dyeing human keratin materials with a lightening effect with a composition comprising, in a cosmetically acceptable medium, at least one fluorescent dye that is soluble in the medium, and at least one surfactant chosen from amphoteric surfactants chosen from betaines and imidazolium derivatives, and from nonionic surfactants chosen from alkylpyrrolidones, oxyalkylenated fatty alcohol ethers, glycerolated fatty alcohol ethers, fatty acid esters of oxyalkylenated monoalcohols, fatty acid esters of glycerolated monoalcohols, fatty acid esters of optionally oxyalkylenated polyols, and fatty acid esters of optionally glycerolated polyols In one aspect of the present disclosure, the amphoteric surfactants of betaine type may be chosen from ($C_8$–$C_{20}$) alkylbetaines, ($C_8$–$C_{20}$)alkylamido($C_1$–$C_8$)alkylbetaines, ($C_8$–$C_{20}$)alkylamido($C_1$–$C_8$)alkylsulfobetaines and sulfobetaines. In one embodiment, the amphoteric surfactants of betaine type are chosen from ($C_8$–$C_{20}$)alkylbetaines, ($C_8$–$C_{20}$)alkylamido($C_1$–$C_8$)alkylsulfobetaines, and sulfobetaines.

Non-limiting examples that may be mentioned include the compounds classified in the CTFA dictionary, 9th edition, 2002, under the names cocobetaine, laurylbetaine, cetylbetaine, coco/oleamidopropylbetaine, cocamidopropylbetaine, palmitamidopropylbetaine, stearamidopropylbetaine, cocamidoethylbetaine, cocamidopropylhydroxysultaine, oleamidopropylhydroxysultaine, cocohydroxysultaine, laurylhydroxysultaine, and cocosultaine, alone or as mixtures.

The imidazolium derivatives according to the present disclosuremay be chosen from amphocarboxyglycinates and amphocarboxypropionates.

Non-limiting examples of imidazolium derivatives that may be mentioned include the compounds classified in the CTFA dictionary, 9th edition, 2002, under the names disodium cocoamphodiacetate, disodium lauroamphodiacetate, disodium caproamphodiacetate, disodium capryloamphodiacetate, disodium cocoamphodipropionate, disodium lauroamphodipropionate, disodium caproamphodipropionate, disodium capryloamphodipropionate, lauroamphodipropionic acid, and cocoamphodipropionic acid, alone or as mixtures.

In one aspect of the present disclosure, nonionic surfactants that may be used in the composition include nonionic alkylpyrrolidones, for example ($C_1$–$C_{30}$)alkyl-pyrrolidones.

Other non-limiting examples that may be mentioned include the compounds classified in the CTFA dictionary, 9th edition, 2002, under the names laurylpyrrolidone, caprylpyrrolidone, and methylpyrrolidone, alone or as mixtures.

In another aspect of the present disclosure, the oxyalkylenated and glycerolated fatty alcohol ethers may be chosen from linear and branched, saturated and unsaturated, ethoxylated and/or propoxylated and/or glycerolated, optionally hydroxylated fatty alcohols, comprising a fatty chain comprising, for example, from 8 to 30 carbon atoms, the number of ethylene oxide and/or propylene oxide groups may range from 1 to 200 and the number of glycerol groups may range from 1 to 30.

In one embodiment, the oxyalkylenated and glycerolated fatty alcohol ethers may be chosen from monoethers and diethers.

Non-limiting examples that may be mentioned include the compounds classified in the CTFA dictionary, 9th edition, 2002, under the names oleyl glyceryl ether, oleth-2, oleth-8, oleth-106, steareth-20, laureth-10, PEG-4 ditallow ether, PPG-beneth-15, PPG-8 ceteth-1, PPG-50 cetyl ether, PPG-6-decyltetradeceth-12, PPG-2-isodeceth-9, PPG-30 isocetyl ether, PPG-4 lauryl ether, and PPG-10 oleyl ether.

In one embodiment, the fatty alcohol ethers are chosen from linear and branched, saturated and unsaturated, ethoxylated and propoxylated, and propoxylated, and/or glycerolated optionally hydroxylated fatty alcohols.

The fatty acid esters of oxyalkylenated and glycerolated monoalcohols and polyols disclosed herein may be chosen from esters of linear and branched, saturated and unsaturated carboxylic acids with a fatty chain comprising, for example, from 8 to 30 carbon atoms.

In one aspect of the present disclosure, where a fatty acid ester of a monoalcohol is present, this monoalcohol may comprise an entity chosen from linear and branched, saturated and unsaturated, ethoxylated and/or propoxylated or glycerolated fatty chains comprising, for example, from 8 to 30 carbon atoms. For example, the number of ethylene oxide or propylene oxide groups in this monoalcohol may range from 1 to 200 and the number of glycerol groups may range from 1 to 30.

In another aspect of the present disclosure, where fatty acid esters of polyols are present, these polyols may be chosen from glycerol, sorbitol, glucose, methylglucose, and sorbitol anhydride, or mixtures thereof. In yet another aspect of the present disclosure, the polyol may be chosen from a polyethylene glycol or a polypropylene glycol.

In another aspect of the present disclosure, the polyol disclosed herein may be oxyalkylenated or glycerolated. If such is the case, the number of ethylene oxide and/or propylene oxide groups of this polyol may range from 1 to 200 and the number of glycerol groups may range from 1 to 30.

Non-limiting examples of these fatty acid esters that may be mentioned include the compounds classified in the CTFA dictionary, 9th edition, 2002, under the names steareth-12 stearate, steareth-5 stearate, PEG-15 oleate, PEG-20 palmitate, PEG-6 isopalmitate, PEG-10 polyglyceryl-2 laurate, PEG-30 glyceryl stearate, PEG-32 dioleate, PEG-30 dipolyhydroxystearate, PEG-8 ditallate, PEG-4 ethylhexanoate, PEG 90 glyceryl isostearate, PEG-15 glyceryl trioleate, PEG-20 methylglucose distearate, PEG-20 sorbitan cocoate, PPG-17 dioleate, methylglucose laurate, methylglucose dioleate, sorbitan palmitate, sorbitan sesquioleate, and sorbitan trioleate.

In one embodiment, the at least one surfactant chosen from amphoteric surfactants and nonionic surfactants, as defined herein, may be present in the composition in an amount ranging from 0.01% to 30% by weight, for example from 0.1% to 20% by weight, and further for example from 0.2% to 10% by weight relative to the total weight of the composition.

In another aspect of the present disclosure, the composition used herein may comprise at least one fluorescent dye.

For the purposes of the present disclosure, the term "fluorescent dye" means a dye which is a molecule that colors by itself, and thus absorbs light in the visible spectrum and possibly in the ultraviolet spectrum (wavelengths ranging from 360 to 760 nanometers), but which, in contrast with a standard dye, converts the absorbed energy into fluorescent light of a longer wavelength emitted in the visible region of the spectrum.

The fluorescent dye present in the composition according to the present disclosure may be differentiated from an optical brightener. Optical brighteners, which may also be known as brighteners, fluorescent brighteners, fluorescent brightening agents, fluorescent whitening agents, whiteners or fluorescent whiteners, are colorless transparent compounds. These compounds do not dye because they do not absorb light in the visible region, but only in the ultraviolet region (for example, wavelengths ranging from 200 to 400 nanometers). They convert the absorbed energy into fluorescent light of a longer wavelength emitted in the visible region of the spectrum; the color impression is then generated solely by purely fluorescent light that is predominantly blue (wavelengths ranging from 400 to 500 nanometers).

In another aspect of the present disclosure, the fluorescent dye used in the composition may be soluble in the medium of the composition. The fluorescent dye differs therein from a fluorescent pigment, which itself is insoluble in the medium of the composition.

In yet another aspect of the present disclosure, the fluorescent dye used in the context of the present disclosure, which may be optionally neutralized, can be soluble in the medium of the composition to at least 0.001 g/l, for example at least 0.5 g/l, further for example at least 1 g/l and, and in yet another example at least 5 g/l, with each of the preceding solubilities corresponding with a temperature of between 15 and 25° C.

In another aspect of the present disclosure, the at least one fluorescent dye forming part of the composition does not comprise three fused rings, wherein one of the rings is a monocationic heterocycle comprising two nitrogen atoms.

In yet another aspect of the present disclosure, the composition does not comprise, as the at least one fluorescent dye, a 2-[2-(4-dialkylamino)phenylethenyl]-1-alkylpyridinium wherein the alkyl radical of the pyridinium nucleus is chosen from methyl and ethyl radicals and that of the benzene nucleus is chosen from methyl radicals, and wherein the counterion is chosen from halides.

In one embodiment, the composition does not comprise, as the at least one fluorescent dye, a compound chosen from azo, azomethine, and methine monocationic heterocyclic fluorescent dyes.

In another embodiment, the at least one fluorescent dye is chosen from dyes in the orange range.

In yet another embodiment of the present disclosure, the at least one fluorescent dye provides a reflectance maximum that is in the wavelength range from 500 to 650 nanometers, for example in the wavelength range from 550 to 620 nanometers.

Other fluorescent dyes according to the present disclosure are compounds that are known per se.

As examples of fluorescent dyes that may be used, non-limiting mention may be made of the fluorescent dyes belonging to the following families: naphthalimides; cationic coumarins; non-cationic coumarins; xanthenodiquinolizines (such as, especially, sulphorhodamines); azaxanthenes; naphtholactams; azlactones; oxazines; thiazines; dioxazines; polycationic fluorescent dyes of azo, azomethine or methine type, alone or as mixtures Among the soluble fluorescent dyes of this type, non-limiting mention may be made of the following:

Brilliant Yellow B6GL sold by the company Sandoz and having the following structure:

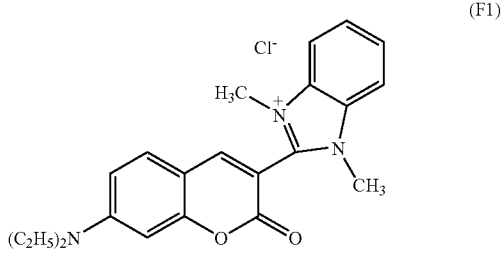

Basic Yellow 2, or Auramine O, sold by the companies Prolabo, Aldrich or Carlo Erba and having the following structure:

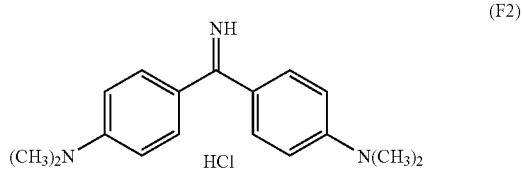

4,4'-(imidocarbonyl)bis(N,N-dimethylaniline) monohydrochloride—CAS number 2465-27-2.

Non-limiting mention may also be made of the compounds comprising the following formula:

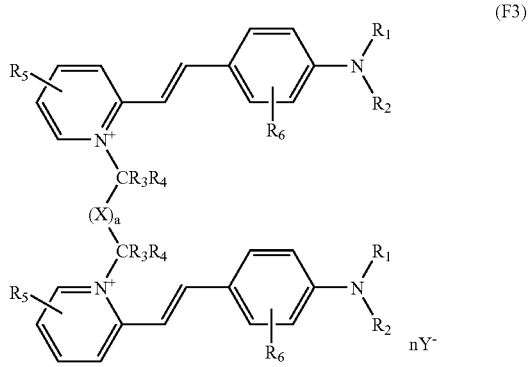

wherein, $R_1$ and $R_2$, which may be identical or different, are chosen from:
a hydrogen atom;
linear and branched alkyl radicals comprising 1 to 10 carbon atoms for example, from 1 to 4 carbon atoms, wherein said alkyl radicals are optionally interrupted and/or substituted with at least one entity chosen from hetero atoms and groups comprising at least one hetero atom and wherein said alkyl radicals are optionally substituted with at least one halogen atom; and aryl or arylalkyl radicals, the aryl group comprising 6 carbon atoms and the alkyl group comprising 1 to 4 carbon atoms; the aryl group optionally being substituted with at least one entity chosen from linear and branched alkyl radicals comprising 1 to 4 carbon atoms, wherein said alkyl radicals are optionally interrupted and/or substituted with at least one entity chosen from hetero atoms and groups comprising at least one hetero atom and wherein said alkyl radicals are optionally substituted with at least one halogen atom;

$R_1$ and $R_2$ may optionally be linked so as to form a heterocycle with the nitrogen atom to which they are attached and may comprise at least one other hetero atom, the heterocycle optionally being substituted with at least one linear or branched alkyl radical, for example, comprising from 1 to 4 carbon atoms, wherein said at least one alkyl radical is optionally interrupted and/or substituted with at least one entity chosen from hetero atoms and groups comprising at least one hetero atom and wherein said at least one alkyl radical is substituted with at least one halogen atom;

$R_1$ or $R_2$ may optionally form a heterocycle comprising the nitrogen atom to which they are attached and one of the carbon atoms of the phenyl group comprising the nitrogen atom;

As used herein, the term "hetero atom" means an oxygen or nitrogen atom.

Among the groups bearing such atoms, non-limiting mention may be made of, hydroxyl, alkoxy, carbonyl, amino, ammonium, amido (—N—CO—), and carboxyl (—O—CO— or —CO—O—) groups.

As used herein, the alkenyl groups may comprise one or more unsaturated carbon-carbon bonds (such as —C═C—), for example only one carbon-carbon double bond.

In this general formula, the radicals $R_1$ and $R_2$, which may be identical or different, are chosen from:

a hydrogen atom;

alkyl radicals comprising 1 to 10 carbon atoms, for example 1 to 6 carbon atoms and further for example, 1 to 4 carbon atoms, wherein said alkyl radicals are optionally interrupted with an oxygen atom or optionally substituted with at least one entity chosen from hydroxyl, amino and ammonium radicals and from chlorine and fluorine atoms; and benzyl and phenyl radicals optionally substituted with an radical chosen from alkyl and alkoxy radicals comprising 1 to 4 carbon atoms, for example 1 or 2 carbon atoms;

together with the nitrogen atom to which they are attached, a heterocyclic radical chosen from pyrrolo, pyrrolidino, imidazolino, imidazolo, imidazolium, pyrazolino, piperazino, morpholino, morpholo, pyrazolo and triazolo radicals, wherein said heterocyclic radical is optionally substituted with at least one linear or branched alkyl radical comprising 1 to 4 carbon atoms, said alkyl radical being optionally interrupted and/or substituted with at least one entity chosen from nitrogen atoms, oxygen atoms, groups bearing a nitrogen atom and groups bearing an oxygen atom.

As used herein, for the amino or ammonium radicals, the radicals borne by the nitrogen atom may be identical or different and may be chosen from a hydrogen atom, $C_1$–$C_{10}$ alkyl radicals, such as $C_1$–$C_4$ alkyl radicals, and arylalkyl radicals wherein the aryl group may comprise 6 carbon atoms and the alkyl group may comprise 1 to 10 carbon atoms, such as 1 to 4 carbon atoms.

According to one embodiment of the present disclosure, the radicals $R_1$ and $R_2$, which may be identical or different, may be chosen from a hydrogen atom; linear and branched $C_1$–$C_6$ alkyl radicals; $C_2$–$C_6$ alkyl radicals substituted with a hydroxyl radical; $C_2$–$C_6$ alkyl radicals bearing an amino or ammonium group; $C_2$–$C_6$ chloroalkyl radicals; $C_2$–$C_6$ alkyl radicals interrupted with an oxygen atom or a group comprising an oxygen atom (for example ester); aromatic radicals, such as phenyl, benzyl and 4-methylphenyl; heterocyclic radicals such as pyrrolo, pyrrolidino, imidazolo, imidazolino, imidazolium, piperazino, morpholo, morpholino, pyrazolo and triazolo radicals, optionally substituted with at least one $C_1$–$C_6$ alkyl or aromatic radicals.

In another embodiment of the present disclosure, the radicals $R_1$ and $R_2$, which may be identical or different, may be chosen from a hydrogen atom, linear and branched $C_1$–$C_6$ alkyl radicals, such as methyl, ethyl, n-butyl, and n-propyl radicals; 2-hydroxyethyl; alkyltrimethylammonium and alkyltriethylammonium radicals, the alkyl radical being a linear $C_2$–$C_6$ alkyl radical; (di)alkylmethylamino and (di)alkylethylamino radicals, the alkyl radical being a linear $C_1$–$C_6$ alkyl radical; —$CH_2CH_2Cl$; —$(CH_2)_n$—$OCH_3$ and —$(CH_2)_n$—$OCH_2CH_3$ with n being an integer ranging from 2 to 6; —$CH_2CH_2$—$OCOCH_3$; and —$CH_2CH_2COOCH_3$.

In one embodiment, the radicals $R_1$ and $R_2$, which may be identical or different, are chosen from methyl radicals and ethyl radicals.

In yet another aspect of the present disclosure, the radicals $R_1$, and $R_2$, which may be identical or different, may also be chosen from heterocyclic radicals of the pyrrolidino, 3-aminopyrrolidino, 3-(dimethyl)aminopyrrolidino, 3-(trimethyl)aminopyrrolidino, 2,5-dimethylpyrrolo, 1H-imidazolo, 4-methylpiperazino, 4-benzylpiperazino, morpholo, 3,5-(tert-butyl)-1H-pyrazolo, 1H-pyrazolo, and 1H-1,2,4-triazolo type.

In another aspect of the present disclosure, the radicals $R_1$ and $R_2$, which may be identical or different, may be linked so as to form a heterocycle of formulae (I) and (II) below:

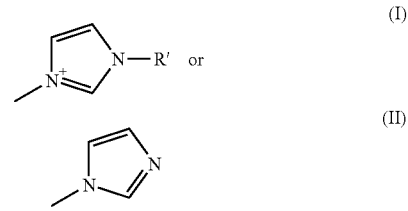

wherein R' is chosen from a hydrogen atom and $C_1$–$C_3$ alkyl radicals, —$CH_2CH_2OH$, —$CH_2CH_2OCH_3$.

In one embodiment of the present disclosure, $R_5$, which may be identical or different, may be chosen from a hydrogen atom, a fluorine atom, a chlorine atom, and linear and branched alkyl radicals comprising 1 to 4 carbon atoms optionally interrupted with an oxygen or nitrogen atom.

For example, the substituent $R_5$, if it is other than hydrogen, may be in position(s) 3 and/or 5 relative to the carbon of the ring bearing the nitrogen substituted with the radicals $R_1$ and $R_2$, for instance, in position 3 relative to that carbon.

In another example, the radicals $R_5$, which may be identical or different, may be chosen from a hydrogen atom; linear and branched $C_1$–$C_4$ alkyl radicals; —O—$R_{51}$ with $R_{51}$ chosen from linear $C_1$–$C_4$ alkyl radicals; —$R_{52}$—O—$CH_3$ wherein $R_{52}$ is chosen from linear $C_2$–$C_3$ alkyl radicals; —$R_{53}$—N($R_{54}$)$_2$ wherein $R_{53}$ may be chosen from linear $C_2$–$C_3$ alkyl radicals and $R_{54}$, which may be identical or different, may be chosen from a hydrogen atom and methyl radicals.

In yet another example, $R_5$, which may be identical or different, may be chosen from a hydrogen atom, a methyl, and a methoxy group. In one embodiment, $R_5$ is a hydrogen atom.

According to one aspect of the present disclosure, the radicals $R_6$, which may be identical or different, are chosen from a hydrogen atom; linear and branched $C_1$–$C_4$ alkyl radicals; —X wherein X is chosen from chlorine, bromine and fluorine atoms; —$R_{61}$—O—$R_{62}$ wherein $R_{61}$ is a linear $C_2$–$C_3$ alkyl radicals and $R_{62}$ is a methyl radical; —$R_{63}$—N($R_{64}$)$_2$ wherein $R_{63}$ is chosen from linear $C_2$–$C_3$ alkyl radicals and $R_{64}$, which may be identical or different, is chosen from a hydrogen atom and methyl radicals; —N($R_{65}$)$_2$ wherein $R_{65}$, which may be identical or different, is chosen from a hydrogen atom and linear $C_2$–$C_3$ alkyl radicals; —NHCOR$_{66}$ wherein $R_{66}$ is chosen from $C_1$–$C_2$ alkyl radicals, $C_1$–$C_2$ chloroalkyl radicals, radicals —$R_{67}$—NH$_2$ and —$R_{67}$—NH(CH$_3$) and —$R_{67}$—N(CH$_3$)$_2$ and —$R_{67}$—N$^+$(CH$_3$)$_3$ and —$R_{67}$—N$^+$(CH$_2$CH$_3$)$_3$, wherein $R_{67}$ is chosen from $C_1$–$C_2$ alkyl radicals.

In one embodiment, the substituent $R_6$, if it is other than hydrogen, may be in position 2 and/or 4 relative to the nitrogen atom of the pyridinium ring, for example, in position 4 relative to that nitrogen atom.

For instance, these radicals $R_6$, which may be identical or different, may be chosen from a hydrogen atom and methyl and ethyl radicals. In one embodiment, $R_6$ is a hydrogen atom.

In another aspect of the present disclosure, the radicals $R_3$ and $R_4$, which may be identical or different, may be chosen from a hydrogen atom and alkyl radicals comprising 1 to 4 carbon atoms, for example a methyl radical. In one embodiment, $R_3$ and $R_4$ each represent a hydrogen atom.

As mentioned above, X may be chosen from:
linear and branched alkyl radicals comprising 1 to 14 carbon atoms and alkenyl radicals comprising 2 to 14 carbon atoms, wherein the alkyl radicals and alkenyl radicals are optionally interrupted and/or substituted with at least one entity chosen from hetero atoms and groups comprising at least one hetero atom and are optionally substituted with at least one halogen atom;
5- or 6-membered heterocyclic radicals optionally substituted with at least one of:
linear and branched alkyl radicals comprising 1 to 14 carbon atoms,
linear and branched aminoalkyl radicals comprising 1 to 4 carbon atoms, optionally substituted with at least one hetero atom; and
halogen atoms;
fused or non-fused aromatic and diaromatic radicals, optionally separated with at least one alkyl radical comprising 1 to 4 carbon atoms, the aromatic and diaromatic radicals optionally being substituted with at least one halogen atom or with at least one alkyl radical comprising 1 to 10 carbon atoms optionally substituted and/or interrupted with at least one entity chosen from hetero atoms and groups comprising at least one hetero atom; and
dicarbonyl radicals.

In one example, the group X may bear at least one cationic charge.

Thus, X may be chosen from linear and branched alkyl radicals comprising 1 to 14 carbon atoms and alkenyl radicals comprising 2 to 14 carbon atoms, wherein the alkyl radicals and alkenyl radicals may be substituted and/or interrupted with at least one entity chosen from oxygen atoms, nitrogen atoms, fluorine atoms, chlorine atoms, and groups comprising at least one hetero atom.

Among the groups of this type, non-limiting mention may be made of hydroxyl, alkoxy (such as $C_1$–$C_4$ alkoxy), amino, ammonium, amido, carbonyl, and carboxyl groups (such as —COO— or —O—CO—), for example those with a radical of alkyloxy type.

In one aspect of the present invention the nitrogen atom, if it is present, may be in a quaternized or non-quaternized form. In this case, the other radical or the other two radicals borne by the quaternized or non-quaternized nitrogen atom may be identical or different and may be a hydrogen atom or a $C_1$–$C_4$ alkyl radical, such as a methyl group.

According to another aspect of the present disclosure, the group X may be chosen from 5- or 6-membered heterocyclic radicals of the imidazolo, pyrazolo, triazino, and pyridino type, optionally substituted with at least one entity chosen from linear and branched alkyl radicals comprising from 1 to 14 carbon atoms, for example 1 to 10 carbon atoms, and further for example from 1 to 4 carbon atoms; with at least one linear or branched aminoalkyl radical comprising 1 to 10 carbon atoms, for example from 1 to 4 carbon atoms, optionally substituted with a group comprising at least one hetero atom (such as a hydroxyl radical), or with a halogen atom. In one embodiment, the amino group may be linked to the heterocycle.

In accordance with another aspect of the present disclosure, the group X may be chosen from aromatic radicals (such as those comprising 6 carbon atoms), and fused and non-fused diaromatic radicals (such as those comprising from 10 to 12 carbon atoms), optionally separated with an alkyl radical comprising 1 to 4 carbon atoms, the aryl radical(s) optionally being substituted with at least one halogen atom and/or with at least one alkyl radical comprising 1 to 10 carbon atoms, for example 1 to 4 carbon atoms, optionally interrupted with at least one entity chosen from oxygen and nitrogen atoms and groups comprising at least one hetero atom (chosen from, for instance, carbonyl, carboxyl, amido, amino and ammonium radicals).

In one example, the aromatic radical, such as a phenyl radical, may be linked to the groups $CR_3R_4$ via bonds in positions 1,2; 1,3; or 1,4 and further for example, in positions 1,3 and 1,4. If the phenyl radical linked via bonds in positions 1,4 bears one or two substituents, this or these substituent(s) may be located, for instance, in position 1,4 relative to one of the groups $CR_3R_4$. If the phenyl radical linked via bonds in positions 1,3 bears one or two substituents, this or these substituents may be located, for instance, in position 1 and/or 3 relative to one of the groups $CR_3R_4$.

In one aspect of the present disclosure, where the radical is diaromatic, it may be, for example, non-fused and comprise two phenyl radicals optionally separated with a single bond (i.e., a carbon of each of the two rings) or with an alkyl radical, such as of $CH_2$ or $C(CH_3)_2$ type. In another example, the aromatic radicals do not bear a substituent. In yet another aspect, the said diaromatic radical may be linked to the groups $CR_3R_4$ via bonds in positions 4,4'.

As examples of groups X that are suitable, non-limiting mention may be made of linear or branched alkyl radicals comprising 1 to 13 carbon atoms, such as methylene, ethylene, propylene, isopropylene, n-butylene, pentylene and hexylene; 2-hydroxypropylene and 2-hydroxy-n-butylene; $C_1$–$C_{13}$ alkylene radicals substituted or interrupted with at least one entity chosen from nitrogen and oxygen atoms and groups comprising at least one hetero atom (hydroxyl, amino, ammonium, carbonyl or carboxyl, for example), such as —$CH_2CH_2OCH_2CH_2$—, 1,6-dideoxy-d-mannitol, —$CH_2N^+(CH_3)_2CH_2$—, —$CH_2CH_2N^+(CH_3)_2$—$(CH_2)_6N^+(CH_3)_2$—$CH_2CH_2$—, CO—CO—, 3,3-dimethyl-pentylene, 2-acetoxyethylene, butylene-1,2,3,4-tetraol; —CH═CH—; aromatic or diaromatic radicals substituted with at least one alkyl radical, with at least one group bearing at least one hetero atom and/or with at least one halogen atom, such as 1,4-phenylene, 1,3-phenylene, 1,2-phenylene, 2,6-fluorobenzene, 4,4'-biphenylene, 1,3-(5-methylbenzene), 1,2-bis(2-methoxy)benzene, bis(4-phenyl) methane, methyl 3,4-benzoate and 1,4-bis(amidomethyl) phenyl; heterocyclic radicals such as pyridine, and derivatives such as 2,6-bispyridine, imidazole, imidazolium or triazine.

According to another embodiment of the present disclosure, X may be chosen from linear and branched $C_1$–$C_{13}$ alkyl radicals; —$CH_2CH(OH)CH_2$—; —$CH_2CH(Cl)CH_2$—; —$CH_2CH_2$—$OCOCH_2$—; —$CH_2CH_2COOCH_2$—; —Ra—O—Rb— with Ra chosen from linear $C_2$–$C_6$ alkyl radicals and Rb chosen from linear $C_1$–$C_2$ alkyl radicals; -Rc-N(Rd)-Re— with Rc chosen from $C_2$–$C_9$ alkyl radicals, Rd chosen from a hydrogen atom and $C_1$–$C_2$ alkyl radicals and Re chosen from $C_1$–$C_6$ alkyl radicals; —Rf—$N^+(Rg)_2$-Rh— with Rf chosen from linear $C_2$–$C_9$ alkyl radicals, Rg, which may be identical, chosen from $C_1$–$C_2$ alkyl radicals, and Rh chosen from linear $C_1$–$C_6$ alkyl radicals; and —CO—CO—.

In another aspect of the present disclosure X may be chosen from imidazole radicals, optionally substituted with at least one alkyl radical comprising 1 to 14 carbon atoms, for example 1 to 10 carbon atoms and in another example 1 to 4 carbon atoms, and in yet another example the divalent radicals having the following formula;

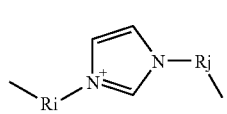

(III)

wherein Ri and Rj, which may be identical or different, may be chosen from linear $C_1$–$C_6$ alkyl radicals;

In another aspect of the present disclosure, X may similarly be chosen from the divalent triazine-based radicals below:

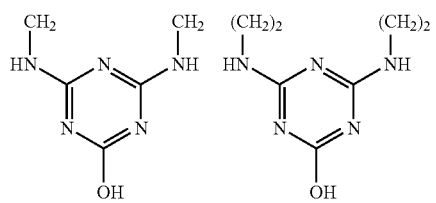

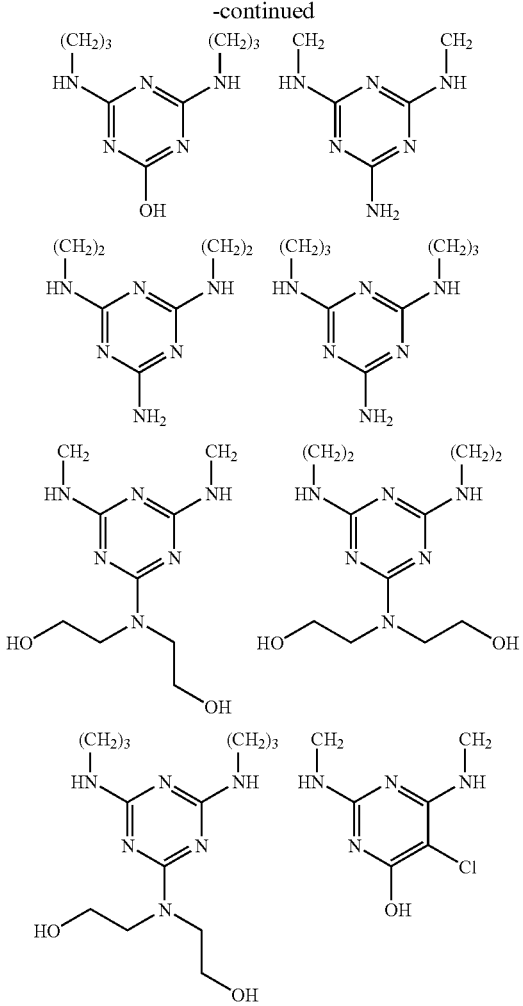

According to yet another embodiment, X may be chosen from the divalent aromatic radicals below:

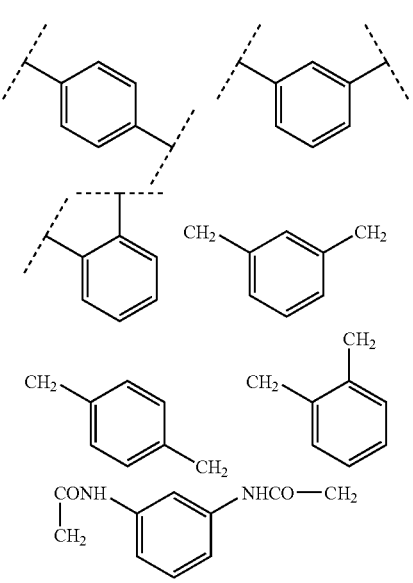

-continued

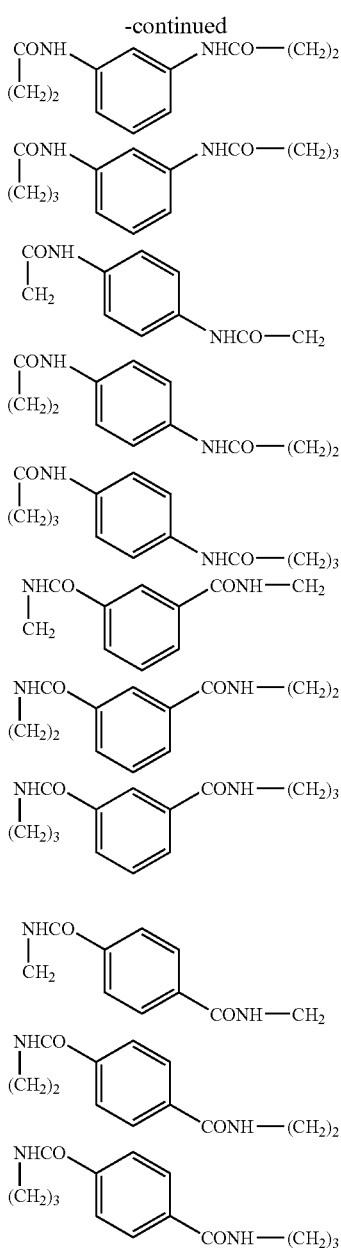

In another aspect of the present disclosure, Y⁻ may be chosen from organic and mineral anions. If there are several anions Y⁻, these anions may be identical or different.

Among the anions of mineral origin, non-limiting mention may be made of anions derived from halogen atoms, such as chlorides, or iodides, sulphates or bisulphates, nitrates, phosphates, hydrogen phosphates, dihydrogen phosphates, carbonates, and bicarbonates.

Among the anions of organic origin, non-limiting mention may be made of anions derived from the salts of saturated or unsaturated, aromatic or non-aromatic monocarboxylic or polycarboxylic, sulphonic or sulphuric acids, optionally substituted with at least one hydroxyl or amino radical, or halogen atoms. Non-limiting examples that are suitable for use include acetates, hydroxyacetates, aminoacetates, (tri) chloroacetates, benzoxyacetates, propionates and derivatives comprising a chlorine atom, fumarates, oxalates, acrylates, malonates, succinates, lactates, tartrates, glycolates, citrates, benzoates and derivatives bearing a methyl or amino radical, alkyl sulphates, tosylates, benzenesulphonates, and toluenesulphonates.

In yet another aspect of the present disclosure, the anions Y, which may be identical or different, may be chosen from chloride, sulphate, methosulphate, and ethosulphate.

In another aspect of the present disclosure, the integer n may be at least equal to 2 and at most equal to the number of cationic charges present in the at least one fluorescent compound.

In yet another aspect of the present disclosure, the fluorescent compounds that have just been described in detail may be symmetrical compounds.

In one embodiment, these compounds may be synthesized by reacting, in a first step, α-picoline with a reagent comprising two leaving groups that may be chosen from halogen atoms, such as bromine, and optionally chlorine, and from tolylsulphonyl and methanesulphonyl groups. This first step may take place in the presence of a solvent, although this is not obligatory, for instance dimethylformamide.

In one example, the number of moles of α-picoline may be in the region of 2 per mole of reagent comprising the leaving groups.

In another example, the reaction may be performed at the reflux temperature of the reagent and/or of the solvent if a solvent is present.

The product derived from this first step may then be placed in contact with a corresponding aldehyde having the following formula:

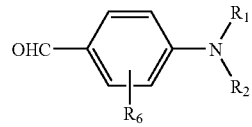

wherein $R_1$, $R_2$ and $R_6$ have the same meanings as indicated above.

In this case also, the reaction may be performed in the presence of a suitable solvent, which, for example, may be at reflux.

In another aspect of the present disclosure the radicals $R_1$ and $R_2$ of the aldehyde may have the meaning indicated in the general formula detailed previously.

In one embodiment, it is also possible to use an aldehyde for which the said radicals represent hydrogen atoms and to perform, in accordance with standard methods, the substitution of these hydrogen atoms with suitable radicals as described in the general formula once the second step is complete.

Reference may be made, for instance, to syntheses as described in U.S. Pat. No. 4,256,458.

In another embodiment of the present disclosure, the composition does not comprise, as fluorescent dye, a compound comprising three fused aromatic nuclei, one of which comprises an oxygen atom.

The at least one fluorescent dye present in the composition according to the present disclosure may be present in the composition in an amount ranging from 0.01% to 20% by weight, for example from 0.05% to 10% by weight, and further for example from 0.1% to 5% by weight, relative to the total weight of the composition.

In a further aspect of the present disclosure, the cosmetically acceptable medium may comprise water or a mixture of water and at least one common organic solvent.

Among the solvents that are suitable for use, non-limiting mention may be made of alcohols such as ethyl alcohol, isopropyl alcohol, benzyl alcohol and phenylethyl alcohol, glycols and glycol ethers, for instance ethylene glycol monomethyl ether, monoethyl ether and monobutyl ether, propylene glycol and ethers thereof, for instance propylene glycol monomethyl ether, butylene glycol, dipropylene glycol and diethylene glycol alkyl ethers, for instance diethylene glycol monoethyl ether or monobutyl ether, or alternatively polyols, for instance glycerol. Polyethylene glycols and polypropylene glycols, and mixtures of all these compounds, may also be used as solvent.

In one embodiment, the common solvents described herein may be present in an amount ranging from 1% to 40% by weight, for example from 5% to 30% by weight relative to the total weight of the composition.

In another embodiment, the pH of the composition in accordance with the present disclosure may range from 3 to 12, for example, from 5 to 11. This pH may be adjusted to a desired value by means of acidifying or basifying agents commonly used in the field.

Non-limiting examples of acidifying agents include mineral or organic acids, for instance hydrochloric acid, orthophosphoric acid, sulphuric acid, carboxylic acids, for instance acetic acid, tartaric acid, citric acid and lactic acid, and sulphonic acids.

Non-limiting examples of basifying agents include aqueous ammonia, alkaline carbonates, alkanolamines such as monoethanolamine, diethanolamine and triethanolamine and derivatives thereof, sodium hydroxide, potassium hydroxide and the compounds of formula (A) below:

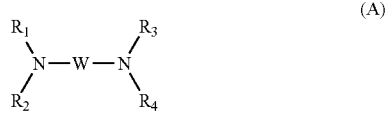

(A)

wherein W is a propylene residue optionally substituted with a hydroxyl group or a $C_1$–$C_6$ alkyl radical; $R_1$, $R_2$, $R_3$ and $R_4$, which may be identical or different, are chosen from a hydrogen atom and $C_1$–$C_6$ alkyl or $C_1$–$C_6$ hydroxyalkyl radicals.

According to one embodiment of the present disclosure, the composition may comprise, in addition to the at least one fluorescent dye, at least one additional non-fluorescent direct dyes of nonionic, cationic or anionic nature.

In one embodiment, the additional direct dyes may be chosen, for example, from nitrobenzene dyes. Further for example, the following red or orange nitrobenzene direct dyes may be suitable for use:
1-hydroxy-3-nitro-4-N-(γ-hydroxypropyl)aminobenzene,
N-(β-hydroxyethyl)amino-3-nitro-4-aminobenzene,
1-amino-3-methyl-4-N-(β-hydroxyethyl)amino-6-nitrobenzene,
1-hydroxy-3-nitro-4-N-(β-hydroxyethyl)aminobenzene,
1,4-diamino-2-nitrobenzene,
1-amino-2-nitro-4-methylaminobenzene,
N-(β-hydroxyethyl)-2-nitro-para-phenylenediamine,
1-amino-2-nitro-4-(β-hydroxyethyl )amino-5-chlorobenzene,
2-nitro-4-aminodiphenylamine,
1-amino-3-nitro-6-hydroxybenzene,
1-(β-aminoethyl)amino-2-nitro-4-(β-hydroxyethyloxy)benzene,
1-(β,γ-dihydroxypropyl)oxy-3-nitro-4-(β-hydroxyethyl) aminobenzene,
1-hydroxy-3-nitro-4-aminobenzene,
1-hydroxy-2-amino-4,6-dinitrobenzene,
1-methoxy-3-nitro-4-(β-hydroxyethyl)aminobenzene,
2-nitro-4'-hydroxydiphenylamine, and
1-amino-2-nitro-4-hydroxy-5-methylbenzene.

In another aspect, the composition in accordance with the present disclosure may also comprise, in addition to or in replacement for these nitrobenzene dyes, at least one additional direct dye chosen from yellow, green-yellow, blue and violet nitrobenzene dyes, azo dyes, anthraquinone dyes, naphthoquinone dyes, benzoquinone dyes, indigoid dyes, and triarylmethane-based dyes.

For example, the at least one additional direct dye may be chosen from basic dyes, among which non-limiting mention may be made of the dyes known in the Color Index, 3rd edition, under the names "Basic Brown 16", "Basic Brown 17", "Basic Yellow 57", "Basic Red 76", "Basic Violet 10", "Basic Blue 26" and "Basic Blue 99"; or acidic direct dyes, among which non-limiting mention may be made of the dyes known in the Colorer Index, 3rd edition, under the names "Acid Orange 7", "Acid Orange 24", "Acid Yellow 36", Acid Red 33", "Acid Red 184", "Acid Black 2", "Acid Violet 43" and "Acid Blue 62", or alternatively cationic direct dyes such as those described in patent applications WO 95/01772, WO 95/15144 and EP-A-0714954, the contents of which relating to such cationic direct dyes are incorporated herein by reference.

Among the additional yellow and green-yellow nitrobenzene direct dyes, non-limiting mention may be made of compounds chosen from:
1-β-hydroxyethyloxy-3-methylamino-4-nitrobenzene,
1-methylamino-2-nitro-5-(β,γ-dihydroxypropyl)oxy benzene,
1-(βhydroxyethyl)amino-2-methoxy-4-nitrobenzene,
1-(β-aminoethyl)amino-2-nitro-5-methoxybenzene,
1,3-di(β-hydroxyethyl)amino-4-nitro-6-chlorobenzene,
1-amino-2-nitro-6-methylbenzene,
1-(β-hydroxyethyl)amino-2-hydroxy-4-nitrobenzene,
N-(βhydroxyethyl)-2-nitro-4-trifluoromethylaniline,
4-(β-hydroxyethyl)amino-3-nitrobenzenesulphonic acid,
4-ethylamino-3-nitrobenzoic acid,
4-(β-hydroxyethyl)amino-3-nitrochlorobenzene,
4-(β-hydroxyethyl)amino-3-nitromethylbenzene,
4-(β,γ-dihydroxypropyl)amino-3-nitrotrifluoromethylbenzene,
1-(β-ureidoethyl)amino-4-nitrobenzene,
1,3-diamino-4-nitrobenzene,
1-hydroxy-2-amino-5-nitrobenzene,
1-amino-2-[tris(hydroxymethyl)methyl]amino-5-nitrobenzene,
1-(β-hydroxyethyl)amino-2-nitrobenzene, and
4-(β-hydroxyethyl)amino-3-nitrobenzamide.

Among the additional blue or violet nitrobenzene direct dyes that may be used, non-limiting mention may be made of compounds chosen from:
1-(β-hydroxyethyl)amino-4-N,N-bis(β-hydroxyethyl) amino-2-nitrobenzene,
1-(γ-hydroxypropyl)amino-4,N,N-bis(β-hydroxyethyl) amino-2-nitrobenzene,
1-(βhydroxyethyl)amino-4-(N-methyl-N-β-hydroxyethyl) amino-2-nitrobenzene, 1-(β-hydroxyethyl)amino-4-(N-ethyl-N-β-hydroxyethyl) amino-2-nitrobenzene, 1-(β,γ-dihydroxypropyl)amino-4-(N-ethyl-N-β-hydroxyethyl)amino-2-nitrobenzene, and 2-nitroparaphenylenediamines having the following formula:

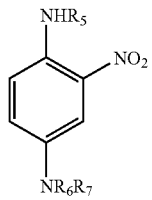

wherein:

$R_6$ is chosen from $C_1$–$C_4$ alkyl radicals and from β-hydroxyethyl, β-hydroxypropyl and γ-hydroxypropyl radicals;

$R_5$ and $R_7$, which may be identical or different, are chosen from β-hydroxyethyl, β-hydroxypropyl, γ-hydroxypropyl and β,γ-dihydroxypropyl radicals, at least one of the radicals $R_6$, $R_7$ or $R_5$ being chosen from γ-hydroxypropyl radicals and $R_6$ and $R_7$ not simultaneously being able to denote a β-hydroxyethyl radical when $R_5$ is a γ-hydroxypropyl radical, such as those described in patent application FR 2,692,572.

When present, the at least one additional direct dye may be present in an amount ranging from 0.0005% to 12% by weight relative to the total weight of the composition, for example from 0.005% to 6% by weight relative to this weight.

In another aspect of the present disclosure, when it is intended for oxidation dyeing, the composition in accordance with the present disclosure comprises, in addition to the at least one fluorescent compound, at least one oxidation base chosen from the oxidation bases conventionally used for oxidation dyeing, among which non-limiting mention may be made of para-phenylenediamines, bis(phenyl)alkylenediamines, para-aminophenols, ortho-aminophenols and heterocyclic bases, and the addition salts thereof with an acid or with an alkaline agent.

Among the para-phenylenediamines that may be used, non-limiting mention may be made of para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxy-ethyl) amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, and 4'-aminophenyl-1-(3-hydroxy)pyrrolidine, and the addition salts thereof with an acid or with an alkaline agent.

In one embodiment, the para-phenylenediamines may be chosen from para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine, and 2-β-acetylaminoethyloxy-para-phenylenediamine, and the addition salts thereof with an acid or with an alkaline agent.

Among the bis(phenyl)alkylenediamines that may be used, non-limiting mention may be made of N,N'-bis(β-hydroxyethyl)-N,N'-bis(4'-aminophenyl)-1,3-diaminopropanol, N,N'-bis(β-hydroxyethyl)-N,N'-bis(4'-aminophenyl) ethylenediamine, N,N'-bis(4-aminophenyl) tetramethylenediamine, N,N'-bis(βhydroxyethyl)-N,N'-bis (4-aminophenyl)tetramethylenediamine, N,N'-bis(4-methylaminophenyl)tetramethylenediamine, N,N'-bis (ethyl)-N,N'-bis(4'-amino-3'-methylphenyl) ethylenediamine, and 1,8-bis(2,5-diaminophenoxy)-3,5-dioxaoctane, and the addition salts thereof with an acid or with an alkaline agent.

Among the para-aminophenols that may be used, non-limiting mention may be made of para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(βhydroxyethylaminomethyl)phenol, and 4-amino-2-fluorophenol, and the addition salts thereof with an acid or with an alkaline agent.

Among the ortho-aminophenols that may be used, non-limiting mention may be made of 2-aminophenol, 2-amino-5-methylphenol, 2-amino-6-methylphenol, and 5-acetamido-2-aminophenol, and the addition salts thereof with an acid or with an alkaline agent.

Among the heterocyclic bases that may be used, non-limiting mention may be made of pyridine derivatives, pyrimidine derivatives, and pyrazole derivatives, and the addition salts thereof with an acid or with an alkaline agent.

When used, the at least one oxidation base may be present in an amount ranging from 0.0005% to 12% by weight, relative to the total weight of the composition, for example from 0.005% to 6% by weight, relative to this weight.

In one aspect of the present disclosure, when it is intended for oxidation dyeing, the composition in accordance with the present disclosure may also comprise, in addition to the at least one fluorescent dye and the at least one oxidation base, at least one coupler so as to modify or to enrich with glints the shades obtained using the at least one fluorescent dye and the at least one oxidation base.

For example, the at least one coupler that may be used in the composition in accordance with the present disclosure may be chosen from the couplers conventionally used in oxidation dyeing, and among which non-limiting mention may be made of meta-phenylenediamines, meta-aminophenols, meta-diphenols, and heterocyclic couplers, and the addition salts thereof with an acid or with an alkaline agent.

Further for example, the at least one coupler may be chosen from 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy) benzene, 2-amino-4-(β-hydroxyethylamino)-1- methoxybenzene, 1,3-diaminobenzene, 1,3-bis(2,4-diaminophenoxy)propane, sesamol, α-naphthol, 6-hydroxyindole, 4-hydroxyindole, 4-hydroxy-N-methylindole, 6-hydroxyindoline, 2,6-dihydroxy-4-methylpyridine, 1H-3-methylpyrazol-5-one, 1-phenyl-3-methylpyrazol-5-one, 2,6-dimethylpyrazolo[1,5-b]-1,2,4-triazole, 2,6-dimethyl[3,2-c]-1,2,4-triazole, and 6-methylpyrazolo[1,5-a]benzimidazole, and the addition salts thereof with an acid or with an alkaline agent.

When present, the at least one coupler may be present in an amount ranging from 0.0001% to 10% by weight relative to the total weight of the composition, for example from 0.005% to 5% by weight relative to this weight.

The addition salts with an acid that may be used in the context of the compositions of the present disclosure (oxidation bases and couplers) may be chosen from the hydrochlorides, hydrobromides, sulphates, citrates, succinates, tartrates, tosylates, benzenesulphonates, lactates, and acetates.

The addition salts with an alkaline agent that may be used in the context of the compositions of the present disclosure (oxidation bases and couplers) may be chosen from the addition salts with alkali metals or alkaline-earth metals, with ammonia, and with organic amines, such as alkanolamines and the compounds of formula (A).

The composition in accordance with the present disclosure may further comprise at least one of various adjuvants conventionally used in compositions, such as anionic, cationic, nonionic, amphoteric or zwitterionic polymers or mixtures thereof, mineral or organic thickeners, antioxidants, penetrating agents, sequestering agents, fragrances, buffers, dispersants, conditioners, for instance cations, cationic or amphoteric polymers, volatile or non-volatile, modified or unmodified silicones, film-forming agents, ceramides, preserving agents, stabilizers and opacifiers.

Among the thickeners that may be used according to the present disclosure, non-limiting mention may be made of thickening systems based on associative polymers that are well known to those skilled in the art, for example those of nonionic, anionic, cationic or amphoteric nature.

Needless to say, a person skilled in the art will take care to select this and other optional additional compounds such that the advantageous properties intrinsically associated with the composition disclosed herein are not, or are not substantially, adversely affected by the envisaged additions.

The composition according to the present disclosure may be in various forms, such as in the forms chosen from liquids, shampoos, creams, gels, and in any other suitable form.

In one embodiment, the composition is in the form of a lightening dye shampoo.

In another embodiment according to the present disclosure, when at least one oxidation base is used, optionally in the presence of at least one coupler, or when the at least one fluorescent dye is used in the context of a lightening direct dyeing, then the composition may further comprise at least one oxidizing agent chosen, for example, from hydrogen peroxide, urea peroxide, alkali metal bromates, persalts such as perborates and persulphates, and enzymes such as peroxidases and two-electron and four-electron oxidoreductases.

In one embodiment, the oxidizing agent is chosen from hydrogen peroxide and enzymes.

The composition described above may be used to dye human keratin materials with a lightening effect.

As used herein the term "human keratin materials" means the skin, the hair, the nails, the eyelashes and the eyebrows, for example, dark skin and artificially colored or pigmented hair.

For the purposes of the present disclosure, the term "dark skin" means a skin whose lightness $L^*$ measured in the CIEL $L^*a^*b^*$ system is less than or equal to 45, for example less than or equal to 40, given that $L^*=0$ is equivalent to black and $L^*=100$ is equivalent to white. For instance, skin types corresponding to this lightness include African skin, afro-American skin, hispano-American skin, Indian skin and North African skin.

For the purposes of the present disclosure, the expression "artificially dyed or pigmented hair" means hair whose tone height is less than or equal to 6 (dark blond), for example less than or equal to 4 (chestnut-brown).

As used herein, the term "hair" will be used without distinction for head hair and also the pilous system (the eyelashes, the eyebrows, etc.).

The lightening of the hair is evaluated by the "tone height," which characterizes the degree or level of lightening. The notion of "tone" is based on the classification of the natural shades, one tone separating each shade from the shade immediately following or preceding it. This definition and the classification of the natural shades are well known to hairstyling professionals and are published in the book "Sciences des traitements capillaires [Hair treatment sciences]" by Charles Zviak, 1988, published by Masson, pp. 215 and 278.

The tone heights range from 1 (black) to 10 (light blond), one unit corresponding to one tone; the higher the figure, the lighter the shade.

Another aspect of the present disclosure is a process of dyeing human keratin fibers, such as hair, with a lightening effect.

In one embodiment, the process of dyeing human keratin fibers with a lightening effect comprises: (a) applying to the human keratin fibers a composition comprising at least one fluorescent dye and at least one surfactant chosen from amphoteric and nonionic surfactants, for a time that is sufficient to develop desired coloration and lightening; (b) optionally rinsing the human keratin fibers; (c) optionally washing the human keratin fibers with shampoo and then rinsing the fibers; and (d) drying or leaving to dry the human keratin fibers.

In another embodiment, the process according to the present disclosure may comprise applying the composition for the time required to develop the coloration and lightening, followed by leaving the hair to dry or drying the hair, without final rinsing.

In yet another embodiment, the process for dyeing and lightening the hair disclosed herein may be performed with a composition as defined herein, in the absence of oxidation dyes and oxidizing agents.

In a further embodiment, the process may be performed with a composition as described herein, in the absence of oxidation dyes, but in the presence of oxidizing agents.

In another embodiment, the dyeing process in accordance with the present disclosure comprises a preliminary step that comprises separately storing a composition comprising, in a cosmetically acceptable medium, at least one fluorescent dye and at least one surfactant chosen from amphoteric and nonionic surfactants, as described herein, and a composition comprising, in a cosmetically acceptable medium, at least one oxidizing agent, and then in mixing them together at the time of use followed by applying this mixture to the hair for a time that is sufficient to develop the desired coloration and lightening, after which the hair may be rinsed, optionally washed with shampoo, rinsed again and dried.

Another aspect of the present disclosure is a process for the oxidation dyeing of the hair using a composition as described herein, in the presence of oxidation dyes. In this embodiment, for example, the dyeing process comprises a preliminary step that comprises separately storing, a composition comprising, in a cosmetically acceptable medium, at least one fluorescent dye and at least one surfactant as described herein and at least one oxidation base, and a composition comprising, in a cosmetically acceptable medium, at least one oxidizing agent, and then in mixing them together at the time of use followed by applying this mixture to the hair for a time that is sufficient to develop the desired coloration, after which the hair may be rinsed, optionally washed with shampoo, rinsed again and dried.

Another aspect of the present disclosure is a multi-compartment device for dyeing and lightening the hair, comprising at least one compartment comprising a composition comprising at least one fluorescent dye and at least one surfactant as described herein, and at least one other compartment comprising a composition comprising at least one oxidizing agent. In one embodiment, this device may be equipped with a means for applying the desired mixture to the hair, such as the devices described in Patent No. FR 2,586,913.

For example, the time required to develop the coloration and to obtain the lightening effect on the hair is from 5 to 60 minutes and further for example, from 5 to 40 minutes.

In another example, the temperature required to develop the coloration and to obtain the lightening effect on the hair may range from room temperature (15 to 25° C.) to 80° C. and further for example from 15 to 40° C.

Another aspect of the present disclosure is a method for dyeing human keratin materials with a lightening effect with a composition comprising, in a cosmetically acceptable medium, at least one fluorescent dye that is soluble in the medium and at least one surfactant chosen from amphoteric surfactants chosen from betaines and imidazolium derivatives, and nonionic surfactants chosen from alkylpyrrolidones, oxyalkylenated fatty alcohol ethers, glycerolated fatty alcohol ethers, fatty acid esters of oxyalkylenated monoalcohols, fatty acid esters of glycerolated monoalcohols, fatty acid esters of optionally oxyalkylenated polyols, and fatty acid esters of optionally glycerolated polyols.

In one embodiment, the at least one fluorescent compound may be chosen from the fluorescent dyes belonging to the following families: naphthalimides; cationic coumarins; non-cationic coumarins; xanthenodiquinolizines (especially such as sulphorhodamines); azaxanthenes; naphtholactams; azlactones; oxazines; thiazines; dioxazines; and monocationic and azo, azomethine and methine polycationic fluorescent dyes.

In a further embodiment, non-limiting mention may be made of compounds of formulae F1, F2 and F3 disclosed herein.

In another embodiment, non-limiting mention may be made of compounds of structure (F4) below:

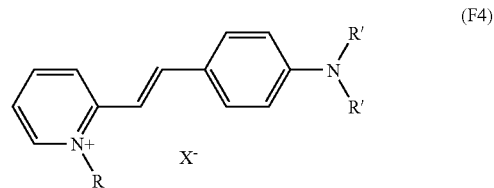

(F4)

wherein R is chosen from methyl and ethyl radicals; R' is chosen from methyl radicals; and X$^-$ is chosen from anions such as chloride, iodide, sulphate, methosulphate, acetate and perchlorate. For example, non-limiting mention may be made of the Photosensitizing Dye NK-557 sold by the company Ubichem, for which R represents an ethyl radical, R' represents a methyl radical and X$^-$ represents an iodide.

Everything described herein regarding the natures and contents of the various additives present in the composition remains valid and will not be repeated in this section.

One aspect of the present disclosure is to obtain treated keratin materials, for example, artificially dyed or pigmented hair, with a reflectance, in the wavelength range from 500 to 700 nanometers and further for example from 540 to 700 nanometers, which may be higher than the reflectance of the same keratin materials not treated in accordance with the present disclosure.

Thus, it may be noted that in the wavelength range from 500 to 700 nanometers, for example from 540 to 700 nanometers, there may be at least one range wherein the reflectance curve corresponding to the treated materials, such as the treated hair, is higher than the reflectance curve corresponding to the untreated materials.

The term "higher than" as used herein means a difference of at least 0.05% for example at least 0.1% of reflectance.

However, it may be noted that there may be, within the wavelength range from 500 to 700 nanometers, for example from 540 to 700 nanometers, one or more ranges wherein the reflectance curve corresponding to the treated materials is either superimposable on or lower than the reflectance curve corresponding to the untreated materials.

In one example, the wavelength at which the difference is maximal between the reflectance curve for the treated materials and that for the untreated materials is in the wavelength range from 500 to 650 nanometers and further for example in the wavelength range from 550 to 620 nanometers.

In one embodiment, the lightening effect is of at least 0.5 tone.

In another embodiment, the use of the compositions according to the disclosure makes it possible to lighten the hair and the skin in a shade which, measured in the CIEL L*a*b* system, has a variable b* of greater than or equal to 6, with a b*/absolute value of a* ratio of greater than 1.2 according to the selection test described below.

Selection Test

The composition was applied to chestnut-brown hair, at a rate of 10 grams of composition per 1 gram of chestnut-brown hair. The composition was spread on so as to cover all of the hair. The composition was left to act for 20 minutes at room temperature (20 to 25° C.). The hair was then rinsed with water and then washed with a shampoo based on lauryl ether sulphate. The hair was then dried. The spectrocolorimetric characteristics of the hair were then measured in order to determine the L*a*b* coordinates.

In the CIEL L*a*b* system, a* and b* indicate two color axes: a* indicates the green/red color axis (+a* is red, −a* is green) and b* indicates the blue/yellow color axis (+b* is yellow and −b* is blue); values close to zero for a* and b* correspond to grey shades.

Other than in the examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained herein. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope are approximations, the numerical values set forth in the specific examples are reported as precisely as possible. Any numerical value, however, inherently contain certain errors necessarily resulting from the standard deviation found in their respective testing measurements. The following examples are intended to illustrate the invention without limiting the scope as a result.

EXAMPLE 1

The two compositions below were prepared in accordance with the present disclosure:

| Composition | 1 | 2 |
|---|---|---|
| Fluorescent dye NK-557 | 0.5% | 0.5% |
| Sodium N-cocoylamidoethyl-N-ethoxy-carboxymethylglycinate (Rhodia Chimie; Miranol C 2M Conc. NP) | — | 2% A.M. |
| Distilled water | qs 100% | qs 100% |

Composition 2 forms part of the present disclosure, while composition 1 serves as a reference.

Each of the compositions was applied to natural chestnut-brown hair (tone height of 4) for 20 minutes at room temperature.

The bath ratio was set at 5.

At the end, the locks were rinsed and dried.

The locks were read using a Varian Cary Eclipse spectrofluorimeter equipped with fibre optics (excitation 480 nm, emission 580 nm, bandwidth 5 nm).

8 measurements were taken along the lock.

The results are collated below:

| | Untreated hair HT4 | Hair HT4 + composition 1 | Hair HT4 + composition 2 |
|---|---|---|---|
| 1st measurement | 0.26 | 55.24 | 59.68 |
| 2nd measurement | 0.17 | 46.69 | 61.43 |
| 3rd measurement | 0.26 | 50.35 | 58.05 |
| 4th measurement | 0.25 | 51.47 | 59.98 |
| 5th measurement | 0.34 | 52.77 | 57.32 |
| 6th measurement | 0.29 | 44.61 | 60.52 |
| 7th measurement | 0.29 | 44.32 | 59.77 |
| 8th measurement | 0.37 | 46.68 | 54.75 |
| Mean | 0.28 | 49.01 | 58.94 |
| Standard deviation | 0.06 | 4.02 | 2.14 |
| Confidence interval (5%) | 0.04 | 2.78 | 1.48 |

It was thus found that the composition of the present disclosure gave a higher fluorescence.

EXAMPLE 2

Fluorescent Compound

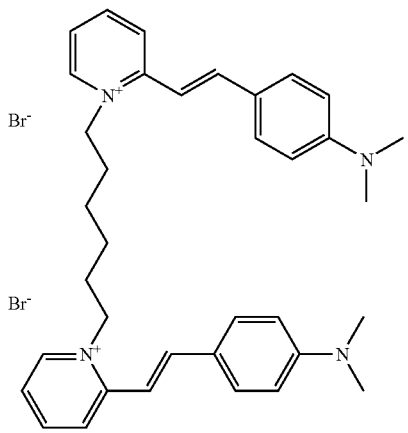

93 g of 2-picoline were reacted with 120 g of 1,6-dibromohexane in dimethylformamide at 110° C. for 5 hours.

The precipitated product was recovered and filtered off.

109 g of the product obtained above were dissolved in methanol and 82.82 g of p-dimethylaminobenzaldehyde were added in two portions, in the presence of pyrrolidine.

The mixture was then left for 30 minutes.

The product was recovered in precipitated form.

Analysis by mass spectroscopy: 266.

Elemental analysis: C, 62.43%; H, 6.40%; Br, 23.07%; N, 8.09%.

The formula was as follows: $C_{36}H_{44}N_4 \cdot 2Br$.

Composition

The composition below was prepared in accordance with the present disclosure:

| | |
|---|---|
| Fluorescent compound | 0.6% |
| Sodium N-cocoylamidoethyl-N-ethoxy-carboxymethylglycinate | 2% |
| Hexylene glycol | 7% |
| Distilled water qs | 100 g |

The percentages are expressed by weight of active material.

Coloration

The composition was applied to a lock of natural chestnut-brown hair (tone height 4) with a leave-in time of 20 minutes.

The locks were then rinsed and dried under a hood for 30 minutes.

A marked lightening effect was obtained on the lock thus treated.

What is claimed is:

1. A method for dyeing human keratin materials having a tone height of less than or equal to 6 with a lightening effect comprising applying to the human keratin materials, in an amount effective to provide a lightening effect on fibers that have a tone height of less than or equal to 6, a composition comprising, in a cosmetically acceptable medium, at least one fluorescent dye that is soluble in the medium and at least one surfactant chosen from:
- amphoteric surfactants chosen from betaines and imidazolium derivatives, and
- nonionic surfactants chosen from alkylpyrrolidones, oxyalkylenated fatty alcohol ethers, glycerolated fatty alcohol ethers, fatty acid esters of oxyalkylenated monoalcohols, fatty acid esters of glycerolated monoalcohols, fatty acid esters of optionally oxyalkylenated polyols, and fatty acid esters of optionally glycerolated polyols;
wherein the at least one fluorescent dye is chosen from groups formed by dyes comprising the following structures:

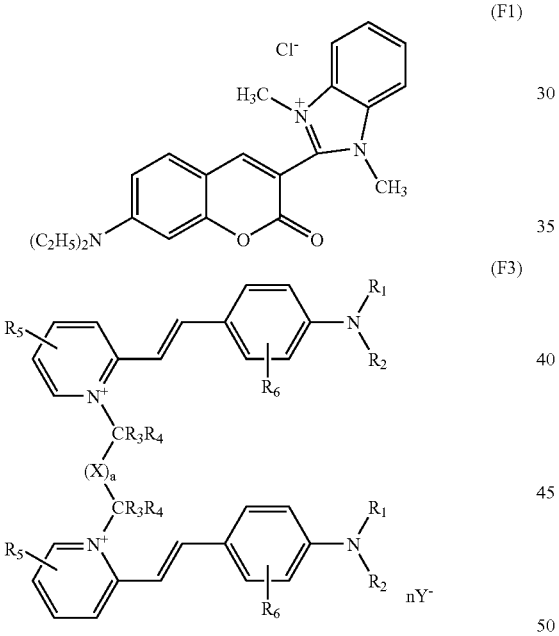

wherein:
$R_1$ and $R_2$, which may be identical or different, are chosen from:
- a hydrogen atom;
- linear and branched alkyl radicals comprising 1 to 10 carbon atoms, optionally interrupted and/or substituted with at least one entity chosen from hetero atoms and groups comprising at least one hetero atom and optionally substituted with at least one halogen atom;
- aryl and arylalkyl radicals, wherein the aryl group comprises 6 carbon atoms and the alkyl group comprises from 1 to 4 carbon atoms; and wherein the aryl group is optionally substituted with at least one alkyl radical chosen from linear and branched alkyl radicals comprising from 1 to 4 carbon atoms, wherein the at least one alkyl radical is optionally interrupted and/or substituted with at least one entity chosen from hetero atoms and groups comprising at least one hetero atom and is optionally substituted with at least one halogen atom;

$R_1$ and $R_2$ may optionally form, together with the nitrogen atom to which they are attached, at least one heterocycle and may comprise at least one other hetero atom, wherein the heterocycle is optionally substituted with at least one alkyl radical chosen from linear and branched alkyl radicals, wherein the at least one alkyl radical is optionally interrupted and/or substituted with at least one entity chosen from hetero atoms and groups comprising at least one hetero atom and is optionally substituted with at least one halogen atom; and $R_1$ or $R_2$ may optionally form, together with the nitrogen to which they are attached and one of the carbon atoms of the phenyl group bearing the nitrogen atom, at least one heterocycle;

$R_3$ and $R_4$, which may be identical or different, are each chosen from a hydrogen atom and alkyl radicals comprising from 1 to 4 carbon atoms;

$R_5$, which may be identical or different, is chosen from a hydrogen atom, a halogen atom and linear and branched alkyl radicals comprising from 1 to 4 carbon atoms, optionally interrupted with at least one hetero atom;

$R_6$, which may be identical or different, is chosen from a hydrogen atom; a halogen atom; linear and branched alkyl radicals comprising from 1 to 4 carbon atoms, wherein the alkyl radicals are optionally substituted and/or interrupted with at least one entity chosen from hetero atoms and groups bearing at least one hetero atom and are optionally substituted with at least one halogen atom;

X is chosen from:
- linear and branched alkyl radicals comprising from 1 to 14 carbon atoms and alkenyl radicals comprising from 2 to 14 carbon atoms, wherein the alkyl radicals and alkenyl radicals are optionally interrupted and/or substituted with at least one entity chosen from hetero atoms and groups comprising at least one hetero atom and are optionally substituted with at least one halogen atom;
- 5- or 6-membered heterocyclic radicals optionally substituted with at least one of:
  - linear and branched alkyl radicals comprising from 1 to 14 carbon atoms, wherein the at least one alkyl radicals are optionally substituted with at least one entity chosen from hetero atoms;
  - linear and branched aminoalkyl radicals comprising from 1 to 4 carbon atoms, optionally substituted with at least one hetero atom; and
  - halogen atoms;
- fused and non-fused aromatic and diaromatic radicals, optionally separated with an alkyl radical comprising from 1 to 4 carbon atoms, wherein the aromatic and diaromatic radicals are optionally substituted with at least one entity chosen from halogen atoms and alkyl radicals comprising from 1 to 10 carbon atoms, said alkyl radicals being optionally substituted and/or interrupted with at least one entity chosen from hetero atoms and groups bearing at least one hetero atom;
- a dicarbonyl radical; and the group X possibly bearing at least one cationic charges;

a being equal to 0 or 1:

Y⁻, which may be identical or different, is chosen from organic and mineral anions; and n is an integer at least equal to 2 and at most equal to the number of cationic charges present in the at least one fluorescent compound;

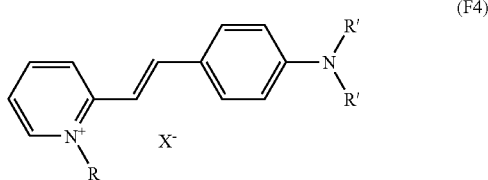

(F4)

wherein R is chosen from methyl and ethyl radicals; R' is chosen from methyl radicals and X⁻ is an anion.

2. The method of claim 1, wherein the human keratin material artificially dyed or pigmented keratin fibers.

3. The method of claim 1, wherein the said human keratin materials have a tone height of less than or equal to 4.

4. The method of claim 1, wherein said lightening effect is of at least 0.5 tone.

5. The method of claim 1, wherein said human keratin material is dark skin.

6. The method of claim 1, wherein the amphoteric surfactants are chosen from betaines chosen from ($C_8$–$C_{20}$) alkylbetaines, ($C_8$–$C_{20}$)alkylamido($C_1$–$C_8$)alkylbetaines, ($C_8$–$C_{20}$)alkylamido($C_1$–$C_8$)alkylsulphobetaines and sulphobetaines.

7. The method of claim 1, wherein the imidazolium derivatives are chosen from at least one of amphocarboxyglycinates and amphocarboxypropionates.

8. The method of claim 1, wherein the alkylpyrrolidones are ($C_1$–$C_{30}$)alkylpyrrolidones.

9. The method of claim 1, wherein the oxyalkylenated and glycerolated fatty alcohol ethers are chosen from linear and branched, saturated and unsaturated, ethoxylated, propoxylated, and glycerolated, optionally hydroxylated fatty alcohols with a chain comprising from 8 to 30 carbon atoms.

10. The method of claim 1 wherein the fatty acid esters of oxyalkylenated and of glycerolated monoalcohols are chosen from esters of linear and branched, saturated and unsaturated carboxylic acids with a fatty chain comprising from 8 to 30 carbon atoms, and from at least one ester chosen from esters of linear and branched, saturated and unsaturated, ethoxylated, propoxylated and glycerolated monoalcohols with a fatty chain comprising from 8 to 30 carbon atoms.

11. The method of claim 1, wherein the oxyalkylenated and glycerolated polyols are chosen from at least one of glycerol, sorbitol, glucose, methylglucose, sorbitol anhydride, polyethylene glycols, and polypropylene glycols.

12. The method of claim 1, wherein the at least one surfactant is present in the composition in an amount ranging from 0.01% to 30% by weight, relative to the total weight of the composition.

13. The method of claim 12, wherein the at least one surfactant is present in the composition in an amount ranging from 0.1% to 20% by weight, relative to the total weight of the composition.

14. The method of claim 13, wherein the at least one surfactant is present in the composition in an amount ranging from 0.2% to 10% by weight relative to the total weight of the composition.

15. The method of claim 1, wherein the at least one fluorescent dye is soluble in the cosmetically acceptable medium to a concentration of at least 0.001 g/l, at a temperature ranging from 15 to 25° C.

16. The method of claim 15, wherein the at least one fluorescent dye is soluble in the cosmetically acceptable medium to a concentration of at least 0.5 g/l, at a temperature ranging from 15 to 25° C.

17. The method of claim 16, wherein the at least one fluorescent dye is soluble in the cosmetically acceptable medium to a concentration of at least 1 g/l, at a temperature ranging from 15 to 25° C.

18. The method of claim 17, wherein the at least one fluorescent dye is soluble in the cosmetically acceptable medium to a concentration of at least 5 g/l, at a temperature ranging from 15 to 25° C.

19. The method of claim 18, wherein the at least one fluorescent dye is a dye in the orange range.

20. The method of claim 1, wherein the at least one fluorescent dye provides a reflectance maximum that is in the wavelength range from 500 to 650 nanometers.

21. The method of claim 20 wherein the at least one fluorescent dye provides a reflectance maximum that is in the wavelength range from 550 to 620 nanometers.

22. The method of claim 1, wherein X— in formula (F4) is chosen from chloride, iodide, sulphate, methasulphate, acetate, and perchlorate anions.

23. The method of claim 1, wherein $R_1$ and $R_2$, which may be identical or different, are each chosen from linear and branched alkyl radicals comprising from 1 to 4 carbon atoms.

24. The method of claim 1, wherein the heterocycle formed from $R_1$ and $R_2$ and the nitrogen to which they are attached, is optionally substituted with at least one linear or branched alkyl radical comprising from 1 to 4 carbon atoms.

25. The method of claim 1, wherein the at least one fluorescent dye is present in the composition in an amount ranging from 0.01% to 20% by weight relative to the total weight of the composition.

26. The method of claim 25, wherein the at least one fluorescent dye is present in the composition in an amount ranging from 0.05% to 10% by weight relative to the total weight of the composition.

27. The method of claim 26, wherein the at least one fluorescent dye is present in the composition in an amount ranging from 0.1% to 5% by weight relative to the total weight of the composition.

28. The method of claim 1, wherein the composition further comprises at least one additional non-fluorescent direct dye chosen from nonionic, cationic and anionic non-fluorescent direct dyes.

29. The method of claim 28, wherein the at least one additional direct dye is chosen from nitrobenzene dyes, azo dyes, anthraquinone, naphthoquinone and benzoquinone dyes, indigoid dyes and triarylmethane-based dyes.

30. The method of claim 28, wherein the at least one additional direct dye is present in the composition in an amount ranging from 0.0005% to 12% by weight relative to the total weight of the composition.

31. The method of claim 30, wherein the at least one additional direct dye is present in the composition in an amount ranging from 0.005% to 6% by weight relative to the total weight of the composition.

32. The method of claim 1, wherein the composition is in the form of a lightening dyeing shampoo.

33. The method of claim 1, wherein the composition comprises at least one oxidation base chosen from para-phenylenediamines, bis(phenyl)alkylenediamines, para-aminophenols, ortho-aminophenols and heterocyclic bases, and the addition salts thereof with an acid or with an alkaline agent.

34. The method of claim 33, wherein the at least one oxidation base is present in the composition in an amount ranging from 0.0005% to 12% by weight relative to the total weight of the composition.

35. The method of claim 34, wherein the at least one oxidation base is present in the composition in an amount ranging from 0.005% to 6% by weight relative to the total weight of the composition.

36. The method of claim 33, wherein the composition further comprises at least one coupler chosen from meta-phenylenediamines, meta-aminophenols, meta-diphenols, and heterocyclic couplers, and the addition salts thereof with an acid or with an alkaline agent.

37. The method of claim 36 wherein the at least one coupler is present in the composition in an amount ranging from 0.0001% to 10% by weight relative to the total weight of the composition.

38. The method of claim 37 wherein the at least one coupler is present in the composition in an amount ranging from 0.005% to 5% by weight relative to the total weight of the composition.

39. The method of claim 1, wherein the composition further comprises at least one oxidizing agent.

40. The method of claim 39, wherein the at least one oxidizing agent is chosen from hydrogen peroxide, urea peroxide, alkali metal bromates, persalts, and enzymes.

41. The method of claim 40, wherein said persalts are chosen from perborate and persulphates.

42. The method of claim 41, wherein said enzymes are chosen from peroxidases and two-electron and four-electron oxidoreductases.

43. The method of claim 40, wherein the at least one oxidizing agent is hydrogen peroxide.

44. A composition, comprising, in a cosmetically acceptable medium:
at least one fluorescent dye that is soluble in the medium, wherein the at least one fluorescent dye does not comprise three fused rings, wherein one of said rings is a monocationic heterocyle comprising two nitrogen atoms; and wherein the at least one fluorescent dye is not 2-[2-(4-dialkylamino)phenylethenyl]-1-alkylpyridinium, wherein the alkyl radical of the pyridinium nucleus is chosen from methyl and ethyl radicals, and that of the benzene nucleus is chosen from methyl radicals, and wherein the counterion is a halide; and wherein the at least one fluorescent dye is not chosen from azomethine fluorescent dyes; and
at least one surfactant chosen from:
amphoteric surfactants chosen from betaines and imidazolium derivatives, and
nonionic surfactants chosen from alkylpyrrolidones, oxyalkylenated fatty alcohol ethers, glycerolated fatty alcohol ethers, fatty acid esters of oxyalkylenated monoalcohols, fatty acid esters of glycerolated monoalcohols, fatty acid esters of optionally oxyalkylenated polyols, and fatty acid esters of optionally glycerolated polyols;
wherein the at least one fluorescent dye is chosen from groups formed by dyes comprising the following structures:

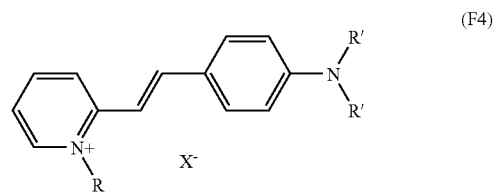
(F4)

wherein:
$R_1$ and $R_2$, which may be identical or different, are chosen from:
a hydrogen atom;
linear and branched alkyl radicals comprising 1 to 10 carbon atoms, optionally interrupted and/or substituted with at least one entity chosen from hetero atoms and groups comprising at least one hetero atom and optionally substituted with at least one halogen atom;
aryl and arylalkyl radicals, wherein the aryl group comprises 6 carbon atoms and the alkyl group comprises from 1 to 4 carbon atoms; and wherein the aryl group is optionally substituted with at least one alkyl radical chosen from linear and branched alkyl radicals comprising from 1 to 4 carbon atoms, wherein the at least one alkyl radical is optionally interrupted and/or substituted with at least one entity chosen from hetero atoms and groups comprising at least one hetero atom and is optionally substituted with at least one halogen atom;
$R_1$ and $R_2$ may optionally form, together with the nitrogen atom to which they are attached, at least one heterocycle and may comprise at least one other hetero atom, wherein the heterocycle is optionally substituted with at least one alkyl radical chosen from linear and branched alkyl radicals, wherein the at least one alkyl radical is optionally interrupted and/or substituted with at least one entity chosen from hetero atoms and groups comprising at least one hetero atom and is optionally substituted with at least one halogen atom; and
$R_1$ or $R_2$ may optionally form, together with the nitrogen to which they are attached and one of the carbon atoms of the phenyl group bearing the nitrogen atom, at least one heterocycle;
$R_3$ and $R_4$, which may be identical or different, are each chosen from a hydrogen atom and alkyl radicals comprising from 1 to 4 carbon atoms;
$R_5$, which may be identical or different, is chosen from a hydrogen atom, a halogen atom and linear and branched alkyl radicals comprising from 1 to 4 carbon atoms, optionally interrupted with at least one hetero atom;
$R_6$, which may be identical or different, is chosen from a hydrogen atom; a halogen atom; linear and branched alkyl radicals comprising from 1 to 4 carbon atoms, wherein the alkyl radicals are optionally substituted and/or interrupted with at least one entity chosen from hetero atoms and groups bearing at least one hetero atom and are optionally substituted with at least one halogen atom;
X is chosen from:
linear and branched alkyl radicals comprising from 1 to 14 carbon atoms and alkenyl radicals comprising from 2 to 14 carbon atoms, wherein the alkyl radicals and alkenyl radicals are optionally interrupted and/or substituted with at least one entity chosen from hetero atoms and groups comprising at least one hetero atom and are optionally substituted with at least one halogen atom;

5- or 6-membered heterocyclic radicals optionally substituted with at least one of:
linear and branched alkyl radicals comprising from 1 to 14 carbon atoms, wherein the at least one alkyl radicals are optionally substituted with at least one entity chosen from hetero atoms;
linear and branched aminoalkyl radicals comprising from 1 to 4 carbon atoms, optionally substituted with at least one hetero atom; and halogen atoms;
fused and non-fused aromatic and diaromatic radicals, optionally separated with an alkyl radical comprising from 1 to 4 carbon atoms, wherein the aromatic and diaromatic radicals are optionally substituted with at least one entity chosen from halogen atoms and alkyl radicals comprising from 1 to 10 carbon atoms, said alkyl radicals being optionally substituted and/or interrupted with at least one entity chosen from hetero atoms and groups bearing at least one hetero atom;
a dicarbonyl radical; and
the group X possibly bearing at least one cationic charges;

a being equal to 0 or 1;

Y⁻, which may be identical or different, is chosen from organic and mineral anions; and n is an integer at least equal to 2 and at most equal to the number of cationic charges present in the at least one fluorescent compound.

45. The composition of claim 44, wherein the at least one fluorescent dye is soluble in the cosmetically acceptable medium of the composition to a concentration of at least 0.001 g/l, at a temperature ranging from 15 to 25° C.

46. The composition of claim 45, wherein the at least one fluorescent dye is soluble in the cosmetically acceptable medium to a concentration of at least 0.5 g/l, at a temperature ranging from 15 to 25° C.

47. The composition of claim 46, wherein the at least one fluorescent dye is soluble in the cosmetically acceptable medium to a concentration of at least 1 g/l, at a temperature ranging from 15 to 25° C.

48. The composition of claim 47, wherein the at least one fluorescent dye is soluble in the cosmetically acceptable medium to a concentration of at least 5 g/l, at a temperature ranging from 15 to 25° C.

49. The composition of claim 44, wherein the at least one fluorescent dye is a dye in the orange range.

50. The composition of claim 44, wherein the at least one fluorescent dye provides a reflectance maximum that is in the wavelength range from 500 to 650 nanometers.

51. The composition of claim 50, wherein the at least one fluorescent dye provides a reflectance maximum that is in the wavelength range from 550 to 620 nanometers.

52. The composition of claim 44, wherein the at least one fluorescent dye is chosen from: naphthalimides; cationic coumarins; non-cationic coumarins; xanthenodiquinolizines; azaxanthenes; naphtholactams; azlactones; oxazines; thiazines; dioxazines; and azo, azomethine, and methine polycationic fluorescent dyes.

53. The composition of claim 44, wherein $R_1$ and $R_2$, which may be identical or different, are each chosen from linear and branched alkyl radicals comprising from 1 to 4 carbon atoms.

54. The composition of claim 44, wherein the heterocycle formed from $R_1$ and $R_2$ and the nitrogen to which they are attached, is optionally substituted with at least one linear or branched alkyl radical comprising from 1 to 4 carbon atoms.

55. The composition of claim 44, wherein the amphoteric surfactants are chosen from betaines chosen from $(C_8–C_{20})$ alkylbetaines, $(C_8–C_{20})$alkylamido$(C_1–C_8)$alkylbetaines, $(C_8–C_{20})$alkylamido$(C_1–C_8)$alkylsulphobetaines and sulphobetaines.

56. The composition of claim 44, wherein the imidazolium derivatives are chosen from amphocarboxyglycinates and amphocarboxypropionates.

57. The composition of claim 44, wherein the nonionic alkylpyrrolidones are chosen from $(C_1–C_{30})$alkylpyrrolidones.

58. The composition of claim 44, wherein the oxyalkylenated or glycerolated fatty alcohol ethers are chosen from linear and branched, saturated and unsaturated, ethoxylated and/or propoxylated or glycerolated, optionally hydroxylated fatty alcohols comprising a chain comprising from 8 to 30 carbon atoms.

59. The composition of claim 44, wherein the fatty acid esters of oxyalkylenated and of glycerolated monoalcohols are chosen from esters of linear and branched, saturated and unsaturated carboxylic acids with a fatty chain comprising from 8 to 30 carbon atoms, and from at least one ester chosen from esters of linear and branched, saturated and unsaturated, ethoxylated, propoxylated and glycerolated monoalcohols with a fatty chain comprising from 8 to 30 carbon atoms.

60. The composition of claim 44, wherein the polyols are chosen from at least one of glycerol, sorbitol, glucose, methylglucose, sorbitol anhydride, polyethylene glycol and polypropylene glycol.

61. The composition of claim 44, wherein the at least one surfactant is present in an amount ranging from 0.01% to 30% by weight relative to the total weight of the composition.

62. The composition of claim 61, wherein the at least one surfactant is present in an amount ranging from 0.1% to 20% by weight relative to the total weight of the composition.

63. The composition of claim 62, wherein the at least one surfactant is present in an amount ranging from 0.2% to 10% by weight relative to the total weight of the composition.

64. The composition of claim 44, wherein the at least one fluorescent dye is present in an amount ranging from 0.01% to 20% by weight relative to the total weight of the composition.

65. The composition of claim 64, wherein the at least one fluorescent dye is present in an amount ranging from 0.05% to 10% by weight relative to the total weight of the composition.

66. The composition of claim 65, wherein the at least one fluorescent dye is present in an amount ranging from 0.1% to 5% by weight relative to the total weight of the composition.

67. The composition of claim 44, further comprising at least one additional non-fluorescent direct dye chosen from nonionic, cationic, and anionic non-fluorescent direct dyes.

68. The composition of claim 67, wherein the at least one additional direct dye is chosen from nitrobenzene dyes, azo dyes, anthraquinone dyes, naphthoquinone dyes, benzoquinone dyes, phenothiazine dyes, indigoid dyes, xanthene dyes, phenanthridine dyes, phthalocyanin dyes, and triarylmethane-based dyes.

69. The composition of claim 67, wherein the at least one additional direct dye is present in an amount ranging from 0.0005% to 12% by weight relative to the total weight of the composition.

70. The composition of claim 69, wherein the at least one additional direct dye is present in an amount ranging from 0.005% to 6% by weight relative to the total weight of the composition.

71. The composition of claim 44, wherein said composition is in the form of a lightening dyeing shampoo.

72. The composition of claim 44, further comprising at least one oxidation base chosen from para-phenylenediamines, bis(phenyl)alkylenediamines, para-aminophenols, ortho-aminophenols and heterocyclic bases, and the addition salts thereof with an acid or with an alkaline agent.

73. The composition of claim 72, wherein the at least one oxidation base is present in an amount ranging from 0.0005% to 12% by weight relative to the total weight of the composition.

74. The composition of claim 73, wherein the at least one oxidation base is present in an amount ranging from 0.005% to 6% by weight relative to the total weight of the composition.

75. The composition of claim 72, further comprising at least one coupler chosen from meta-phenylenediamines, meta-aminophenols, meta-diphenols, heterocyclic couplers, and the addition salts thereof with an acid or with an alkaline agent.

76. The composition of claim 75, wherein the at least one coupler is present in an amount ranging from 0.0001% to 10% by weight relative to the total weight of the dye composition.

77. The composition of claim 76, wherein the at least one coupler is present in an amount ranging from 0.005% to 5% by weight relative to the total weight of the dye composition.

78. The composition of claim 44, further comprising at least one oxidizing agent.

79. The composition of claim 78, wherein the at least one oxidizing agent is chosen from hydrogen peroxide, urea peroxide, alkali metal bromates, persalts, and enzymes.

80. The composition of claim 79, wherein the persalts are chosen from perborates and persulphates.

81. The composition of claim 79, wherein the enzymes are chosen from peroxidases and two-electron and four-electron oxidoreductases.

82. A process for dyeing human keratin fibers with a lightening effect, comprising:
   a) applying to said human keratin fibers for a time that is sufficient to develop a desired coloration and lightening, a composition, comprising, in a cosmetically acceptable medium:
      at least one fluorescent dye that is soluble in the medium; wherein the at least one fluorescent dye does not comprise three fused rings, wherein one of said rings is a monocationic heterocycle comprising two nitrogen atoms; and further wherein the at least one fluorescent dye is not 2-[2-(4-dialkylamino)phenylethenyl]-1-alkylpyridinium, wherein the alkyl radical of the pyridinium nucleus is chosen from methyl and ethyl radicals, and that of the benzene nucleus is chosen from methyl radicals, and wherein the counterion is a halide; and wherein the at least one fluorescent dye is not chosen from azomethine fluorescent dyes; and
   at least one surfactant chosen from:
   amphoteric surfactants chosen from betaines and imidazolium derivatives, and
   nonionic surfactants chosen from alkylpyrrolidones, oxyalkylenated fatty alcohol ethers, glycerolated fatty alcohol ethers, fatty acid esters of oxyalkylenated monoalcohols, fatty acid esters of glycerolated monoalcohols, fatty acid esters of optionally oxyalkylenated polyols, and fatty acid esters of optionally glycerolated polyols,
   b) optionally rinsing the human keratin fibers,
   c) optionally washing the human keratin fibers with shampoo and rinsing the human keratin fibers, and
   d) drying the human keratin fibers or leaving the human keratin fibers to dry; wherein the at least one fluorescent dye is chosen from groups formed by dyes comprising the following structures:

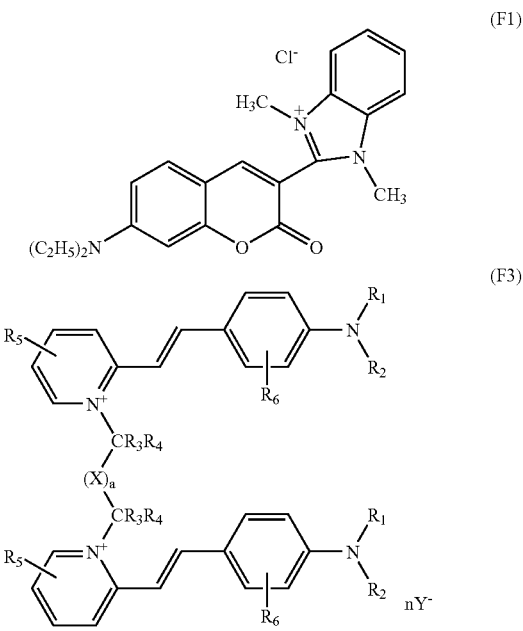

wherein:
   $R_1$ and $R_2$, which may be identical or different, are chosen from:
      a hydrogen atom;
      linear and branched alkyl radicals comprising 1 to 10 carbon atoms, optionally interrupted and/or substituted with at least one entity chosen from hetero atoms and groups comprising at least one hetero atom and optionally substituted with at least one halogen atom;
      aryl and arylalkyl radicals, wherein the aryl group comprises 6 carbon atoms and the alkyl group comprises from 1 to 4 carbon atoms; and wherein the aryl group is optionally substituted with at least one alkyl radical chosen from linear and branched alkyl radicals comprising from 1 to 4 carbon atoms, wherein the at least one alkyl radical is optionally interrupted and/or substituted with at least one entity chosen from hetero atoms and groups comprising at least one hetero atom and is optionally substituted with at least one halogen atom;

R₁ and R₂ may optionally form, together with the nitrogen atom to which they are attached, at least one heterocycle and may comprise at least one other hetero atom, wherein the heterocycle is optionally substituted with at least one alkyl radical chosen from linear and branched alkyl radicals, wherein the at least one alkyl radical is optionally interrupted and/or substituted with at least one entity chosen from hetero atoms and groups comprising at least one hetero atom and is optionally substituted with at least one halogen atom; and R₁ or R₂ may optionally form, together with the nitrogen to which they are attached and one of the carbon atoms of the phenyl group bearing the nitrogen atom, at least one heterocycle;

R₃ and R₄, which may be identical or different, are each chosen from a hydrogen atom and alkyl radicals comprising from 1 to 4 carbon atoms;

R₅, which may be identical or different, is chosen from a hydrogen atom, a halogen atom and linear and branched alkyl radicals comprising from 1 to 4 carbon atoms, optionally interrupted with at least one hetero atom;

R₆, which may be identical or different, is chosen from a hydrogen atom; a halogen atom; linear and branched alkyl radicals comprising from 1 to 4 carbon atoms, wherein the alkyl radicals are optionally substituted and/or interrupted with at least one entity chosen from hetero atoms and groups bearing at least one hetero atom and are optionally substituted with at least one halogen atom;

X is chosen from:
  linear and branched alkyl radicals comprising from 1 to 14 carbon atoms and alkenyl radicals comprising from 2 to 14 carbon atoms, wherein the alkyl radicals and alkenyl radicals are optionally interrupted and/or substituted with at least one entity chosen from hetero atoms and groups comprising at least one hetero atom and are optionally substituted with at least one halogen atom;
  5- or 6-membered heterocyclic radicals optionally substituted with at least one of:
    linear and branched alkyl radicals comprising from 1 to 14 carbon atoms, wherein the at least one alkyl radicals are optionally substituted with at least one entity chosen from hetero atoms;
    linear and branched aminoalkyl radicals comprising from 1 to 4 carbon atoms, optionally substituted with at least one hetero atom; and
    halogen atoms;
  fused and non-fused aromatic and diaromatic radicals, optionally separated with an alkyl radical comprising from 1 to 4 carbon atoms, wherein the aromatic and diaromatic radicals are optionally substituted with at least one entity chosen from halogen atoms and alkyl radicals comprising from 1 to 10 carbon atoms, said alkyl radicals being optionally substituted and/or interrupted with at least one entity chosen from hetero atoms and groups bearing at least one hetero atom;
  a dicarbonyl radical; and
  the group X possibly bearing at least one cationic charges;

a being equal to 0 or 1;

Y⁻, which may be identical or different, is chosen from organic and mineral anions; and n is an integer at least equal to 2 and at most equal to the number of cationic charges present in the at least one fluorescent compound.

83. A process for dyeing human keratin fibers with a lightening effect, comprising:
  a) separately storing
    (1) a composition comprising, in a cosmetically acceptable medium:
    at least one fluorescent dye that is soluble in the medium, wherein the at least one fluorescent dye does not comprise three fused rings, wherein one of said rings is a monocationic heterocycle comprising two nitrogen atoms; and further wherein the at least one fluorescent dye is not 2-[2-(4-dialkylamino)phenylethenyl]-1-alkylpyridinium, wherein the alkyl radical of the pyridinium nucleus is chosen from methyl and ethyl radicals, and that of the benzene nucleus is chosen from methyl radicals, and wherein the counterion is a halide, and wherein the at least one fluorescent dye is not chosen from azomethine fluorescent dyes; and
    at least one surfactant chosen from
    amphoteric surfactants chosen from betaines and imidazolium derivatives, and
    nonionic surfactants chosen from alkylpyrrolidones, oxyalkylenated fatty alcohol ethers, glycerolated fatty alcohol ethers, fatty acid esters of oxyalkylenated monoalcohols, fatty acid esters of glycerolated monoalcohols, fatty acid esters of optionally oxyalkylenated polyols, and fatty acid esters of optionally glycerolated polyols
    optionally at least one additional direct dye, and
    optionally at least one oxidation base optionally combined with at least one coupler; and
    (2) a composition comprising, in a cosmetically acceptable medium, at least one oxidizing agent; and
  b) mixing the separately stored compositions together at the time of use,
  c) applying the mixture to said human keratin fibers for a time that is sufficient to develop a desired coloration and lightening,
  d) optionally rinsing the human keratin fibers,
  e) optionally washing the human keratin fibers with shampoo and rinsing the human keratin fibers, and
  f) drying the human keratin fibers or leaving the human keratin fibers to dry; wherein the at least one fluorescent dye is chosen from groups formed by dyes comprising the following structures:

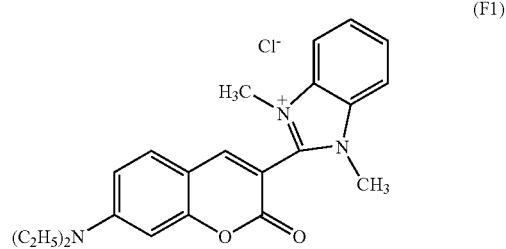

(F1)

-continued

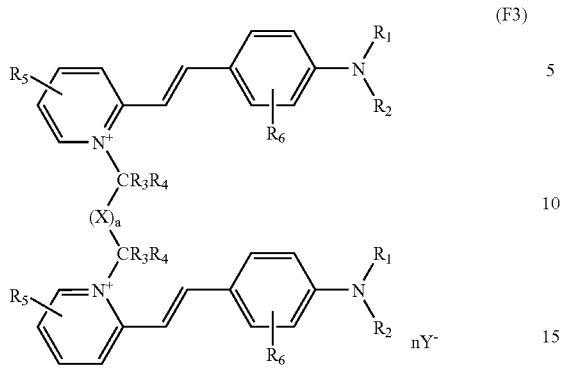

(F3)

wherein:

R₁ and R₂, which may be identical or different, are chosen from:
a hydrogen atom;
linear and branched alkyl radicals comprising 1 to 10 carbon atoms, optionally interrupted and/or substituted with at least one entity chosen from hetero atoms and groups comprising at least one hetero atom and optionally substituted with at least one halogen atom;
aryl and arylalkyl radicals, wherein the aryl group comprises 6 carbon atoms and the alkyl group comprises from 1 to 4 carbon atoms; and wherein the aryl group is optionally substituted with at least one alkyl radical chosen from linear and branched alkyl radicals comprising from 1 to 4 carbon atoms, wherein the at least one alkyl radical is optionally interrupted and/or substituted with at least one entity chosen from hetero atoms and groups comprising at least one hetero atom and is optionally substituted with at least one halogen atom;
R₁ and R₂ may optionally form, together with the nitrogen atom to which they are attached, at least one heterocycle and may comprise at least one other hetero atom, wherein the heterocycle is optionally substituted with at least one alkyl radical chosen from linear and branched alkyl radicals, wherein the at least one alkyl radical is optionally interrupted and/or substituted with at least one entity chosen from hetero atoms and groups comprising at least one hetero atom and is optionally substituted with at least one halogen atom; and
R₁ or R₂ may optionally form, together with the nitrogen to which they are attached and one of the carbon atoms of the phenyl group bearing the nitrogen atom, at least one heterocycle;
R₃ and R₄, which may be identical or different, are each chosen from a hydrogen atom and alkyl radicals comprising from 1 to 4 carbon atoms;
R₅, which may be identical or different, is chosen from a hydrogen atom, a halogen atom and linear and branched alkyl radicals comprising from 1 to 4 carbon atoms, optionally interrupted with at least one hetero atom;
R₆, which may be identical or different, is chosen from a hydrogen atom; a halogen atom; linear and branched alkyl radicals comprising from 1 to 4 carbon atoms, wherein the alkyl radicals are optionally substituted and/or interrupted with at least one entity chosen from hetero atoms and groups bearing at least one hetero atom and are optionally substituted with at least one halogen atom;

X is chosen from:
linear and branched alkyl radicals comprising from 1 to 14 carbon atoms and alkenyl radicals comprising from 2 to 14 carbon atoms, wherein the alkyl radicals and alkenyl radicals are optionally interrupted and/or substituted with at least one entity chosen from hetero atoms and groups comprising at least one hetero atom and are optionally substituted with at least one halogen atom;
5- or 6-membered heterocyclic radicals optionally substituted with at least one of:
linear and branched alkyl radicals comprising from 1 to 14 carbon atoms, wherein the at least one alkyl radicals are optionally substituted with at least one entity chosen from hetero atoms;
linear and branched aminoalkyl radicals comprising from 1 to 4 carbon atoms, optionally substituted with at least one hetero atom; and
halogen atoms;
fused and non-fused aromatic and diaromatic radicals, optionally separated with an alkyl radical comprising from 1 to 4 carbon atoms, wherein the aromatic and diaromatic radicals are optionally substituted with at least one entity chosen from halogen atoms and alkyl radicals comprising from 1 to 10 carbon atoms, said alkyl radicals being optionally substituted and/or interrupted with at least one entity chosen from hetero atoms and groups bearing at least one hetero atom;
a dicarbonyl radical; and
the group X possibly bearing at least one cationic charges;
a being equal to 0 or 1;
Y⁻, which may be identical or different, is chosen from organic and mineral anions; and n is an integer at least equal to 2 and at most equal to the number of cationic charges present in the at least one fluorescent compound.

84. The process according to claim 82, wherein the human keratin fibers are artificially dyed or pigmented.

85. A process for coloring dark skin with a lightening effect, comprising:
(a) applying to the skin a composition, comprising, in a cosmetically acceptable medium:
at least one fluorescent dye that is soluble in the medium, wherein the at least one fluorescent dye does not comprise three fused rings, wherein one of said rings is a monocationic heterocycle comprising two nitrogen atoms; and further wherein the at least one fluorescent dye is not 2-[2-(4-dialkylamino)phenylethenyl]-1-alkylpyridinium, wherein the alkyl radical of the pyridinium nucleus is chosen from methyl and ethyl radicals, and that of the benzene nucleus is chosen from methyl radicals, and wherein the counterion is a halide, and wherein the at least one fluorescent dye is not chosen from azomethine fluorescent dyes; and
at least one surfactant chosen from:
amphoteric surfactants chosen from betaines and imidazolium derivatives, and
nonionic surfactants chosen from alkylpyrrolidones, oxyalkylenated fatty alcohol ethers, glycerolated fatty alcohol ethers, fatty acid esters of oxyalkylenated monoalcohols, fatty acid esters of glycerolated monoalcohols, fatty acid esters of optionally oxyalkylenated polyols, and fatty acid esters of optionally glycerolated polyols (b) drying the skin or leaving the skin to dry; wherein the at least one fluorescent dye is chosen from groups formed by dyes comprising the following structures:

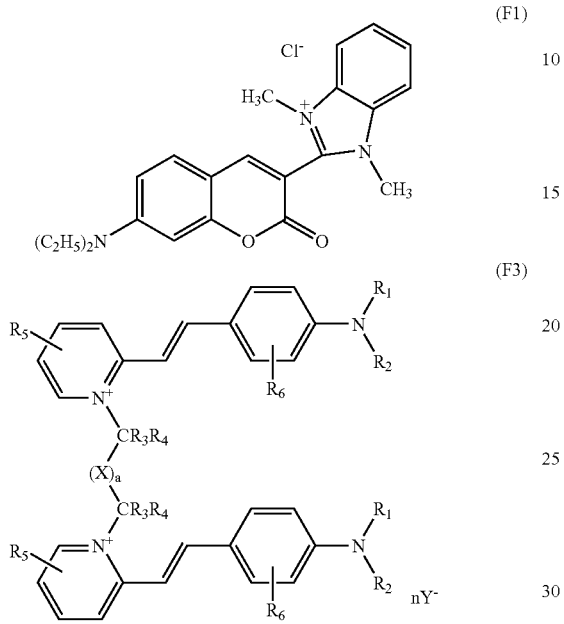

wherein:

$R_1$ and $R_2$, which may be identical or different, are chosen from:
- a hydrogen atom;
- linear and branched alkyl radicals comprising 1 to 10 carbon atoms, optionally interrupted and/or substituted with at least one entity chosen from hetero atoms and groups comprising at least one hetero atom and optionally substituted with at least one halogen atom;
- aryl and arylalkyl radicals, wherein the aryl group comprises 6 carbon atoms and the alkyl group comprises from 1 to 4 carbon atoms; and wherein the aryl group is optionally substituted with at least one alkyl radical chosen from linear and branched alkyl radicals comprising from 1 to 4 carbon atoms, wherein the at least one alkyl radical is optionally interrupted and/or substituted with at least one entity chosen from hetero atoms and groups comprising at least one hetero atom and is optionally substituted with at least one halogen atom;

$R_1$ and $R_2$ may optionally form, together with the nitrogen atom to which they are attached, at least one heterocycle and may comprise at least one other hetero atom, wherein the heterocycle is optionally substituted with at least one alkyl radical chosen from linear and branched alkyl radicals, wherein the at least one alkyl radical is optionally interrupted and/or substituted with at least one entity chosen from hetero atoms and groups comprising at least one hetero atom and is optionally substituted with at least one halogen atom; and $R_1$ or $R_2$ may optionally form, together with the nitrogen to which they are attached and one of the carbon atoms of the phenyl group bearing the nitrogen atom, at least one heterocycle;

$R_3$ and $R_4$, which may be identical or different, are each chosen from a hydrogen atom and alkyl radicals comprising from 1 to 4 carbon atoms;

$R_5$, which may be identical or different, is chosen from a hydrogen atom, a halogen atom and linear and branched alkyl radicals comprising from 1 to 4 carbon atoms, optionally interrupted with at least one hetero atom;

$R_6$, which may be identical or different, is chosen from a hydrogen atom; a halogen atom; linear and branched alkyl radicals comprising from 1 to 4 carbon atoms, wherein the alkyl radicals are optionally substituted and/or interrupted with at least one entity chosen from hetero atoms and groups bearing at least one hetero atom and are optionally substituted with at least one halogen atom;

X is chosen from:
- linear and branched alkyl radicals comprising from 1 to 14 carbon atoms and alkenyl radicals comprising from 2 to 14 carbon atoms, wherein the alkyl radicals and alkenyl radicals are optionally interrupted and/or substituted with at least one entity chosen from hetero atoms and groups comprising at least one hetero atom and are optionally substituted with at least one halogen atom;
- 5- or 6-membered heterocyclic radicals optionally substituted with at least one of:
  - linear and branched alkyl radicals comprising from 1 to 14 carbon atoms, wherein the at least one alkyl radicals are optionally substituted with at least one entity chosen from hetero atoms;
  - linear and branched aminoalkyl radicals comprising from 1 to 4 carbon atoms, optionally substituted with at least one hetero atom; and
  - halogen atoms;
- fused and non-fused aromatic and diaromatic radicals, optionally separated with an alkyl radical comprising from 1 to 4 carbon atoms, wherein the aromatic and diaromatic radicals are optionally substituted with at least one entity chosen from halogen atoms and alkyl radicals comprising from 1 to 10 carbon atoms, said alkyl radicals being optionally substituted and/or interrupted with at least one entity chosen from hetero atoms and groups bearing at least one hetero atom;
- a dicarbonyl radical; and
- the group X possibly bearing at least one cationic charges;

a being equal to 0 or 1;

$Y^-$, which may be identical or different, is chosen from organic and mineral anions; and n is an integer at least equal to 2 and at most equal to the number of cationic charges present in the at least one fluorescent compound.

86. A multi-compartment device for dyeing and lightening the hair, comprising:
- at least one compartment comprising a composition, comprising, in a cosmetically acceptable medium:
  - at least one fluorescent dye that is soluble in the medium, wherein the at least one fluorescent dye does not comprise three fused rings, wherein one of said rings is a monocationic heterocycle comprising two nitrogen atoms; and further wherein the at least one fluorescent dye is not 2-[2-(4-dialkylamino)phenylethenyl]-1-alkylpyridinium, wherein the alkyl radical of the pyridinium nucleus is chosen from methyl and ethyl radicals, and that of the benzene nucleus is chosen from methyl radicals, and wherein the counterion is a halide, and wherein the at least one fluorescent dye is not chosen from azomethine fluorescent dyes; and at least one surfactant chosen from:

amphoteric surfactants chosen from betaines and imidazolium derivatives, and nonionic surfactants chosen from alkylpyrrolidones, oxyalkylenated fatty alcohol ethers, glycerolated fatty alcohol ethers, fatty acid esters of oxyalkylenated monoalcohols, fatty acid esters of glycerolated monoalcohols, fatty acid esters of optionally oxyalkylenated polyols, and fatty acid esters of optionally glycerolated polyols, optionally at least one additional direct dye, and optionally at least one oxidation base optionally combined with at least one coupler;

and at least one other compartment comprising a composition comprising at least one oxidizing agent; wherein the at least one fluorescent dye is chosen from groups formed by dyes comprising the following structures:

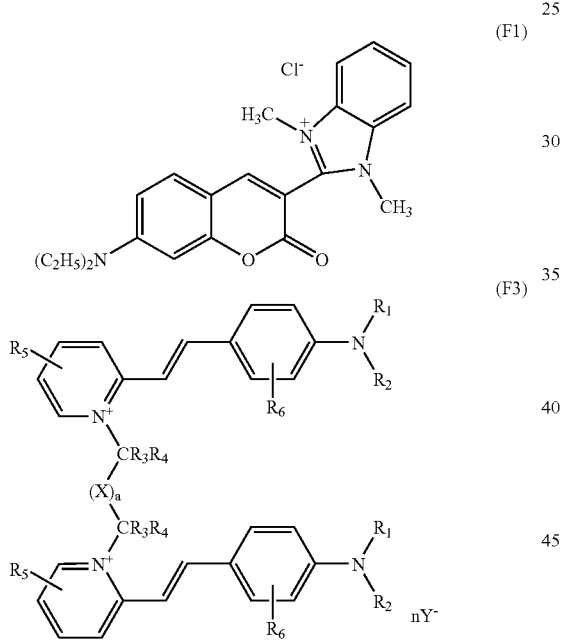

wherein:

$R_1$ and $R_2$, which may be identical or different, are chosen from:

a hydrogen atom;

linear and branched alkyl radicals comprising 1 to 10 carbon atoms, optionally interrupted and/or substituted with at least one entity chosen from hetero atoms and groups comprising at least one hetero atom and optionally substituted with at least one halogen atom;

aryl and arylalkyl radicals, wherein the aryl group comprises 6 carbon atoms and the alkyl group comprises from 1 to 4 carbon atoms; and wherein the aryl group is optionally substituted with at least one alkyl radical chosen from linear and branched alkyl radicals comprising from 1 to 4 carbon atoms, wherein the at least one alkyl radical is optionally interrupted and/or substituted with at least one entity chosen from hetero atoms and groups comprising at least one hetero atom and is optionally substituted with at least one halogen atom;

$R_1$ and $R_2$ may optionally form, together with the nitrogen atom to which they are attached, at least one heterocycle and may comprise at least one other hetero atom, wherein the heterocycle is optionally substituted with at least one alkyl radical chosen from linear and branched alkyl radicals, wherein the at least one alkyl radical is optionally interrupted and/or substituted with at least one entity chosen from hetero atoms and groups comprising at least one hetero atom and is optionally substituted with at least one halogen atom; and $R_1$ or $R_2$ may optionally form, together with the nitrogen to which they are attached and one of the carbon atoms of the phenyl group bearing the nitrogen atom, at least one heterocycle;

$R_3$ and $R_4$, which may be identical or different, are each chosen from a hydrogen atom and alkyl radicals comprising from 1 to 4 carbon atoms;

$R_5$, which may be identical or different, is chosen from a hydrogen atom, a halogen atom and linear and branched alkyl radicals comprising from 1 to 4 carbon atoms, optionally interrupted with at least one hetero atom;

$R_6$, which may be identical or different, is chosen from a hydrogen atom; a halogen atom; linear and branched alkyl radicals comprising from 1 to 4 carbon atoms, wherein the alkyl radicals are optionally substituted and/or interrupted with at least one entity chosen from hetero atoms and groups bearing at least one hetero atom and are optionally substituted with at least one halogen atom;

X is chosen from:

linear and branched alkyl radicals comprising from 1 to 14 carbon atoms and alkenyl radicals comprising from 2 to 14 carbon atoms, wherein the alkyl radicals and alkenyl radicals are optionally interrupted and/or substituted with at least one entity chosen from hetero atoms and groups comprising at least one hetero atom and are optionally substituted with at least one halogen atom;

5- or 6-membered heterocyclic radicals optionally substituted with at least one of:

linear and branched alkyl radicals comprising from 1 to 14 carbon atoms, wherein the at least one alkyl radicals are optionally substituted with at least one entity chosen from hetero atoms;

linear and branched aminoalkyl radicals comprising from 1 to 4 carbon atoms, optionally substituted with at least one hetero atom; and halogen atoms;

fused and non-fused aromatic and diaromatic radicals, optionally separated with an alkyl radical comprising from 1 to 4 carbon atoms, wherein the aromatic and diaromatic radicals are optionally substituted with at least one entity chosen from halogen atoms and alkyl radicals comprising from 1 to 10 carbon atoms, said alkyl radicals being optionally substituted and/or interrupted with at least one entity chosen from hetero atoms and groups bearing at least one hetero atom;

a dicarbonyl radical; and the group X possibly bearing at least one cationic charges;

a being equal to 0 or 1;

$Y^-$, which may be identical or different, is chosen from organic and mineral anions; and n is an integer at least equal to 2 and at most equal to the number of cationic charges present in the at least one fluorescent compound.

* * * * *

UNITED STATES PATENT AND TRADEMARK OFFICE
CERTIFICATE OF CORRECTION

PATENT NO. : 7,198,650 B2  
APPLICATION NO. : 10/814338  
DATED : April 3, 2007  
INVENTOR(S) : Chrystel Pourille-Grethen and Grégory Plos Page 1 of 2

It is certified that error appears in the above-identified patent and that said Letters Patent is hereby corrected as shown below:

In claim 1, column 27, line 3, "1:" should read --1;--.

In claim 2, column 27, line 23, "material artificially" should read --material is chosen from artificially--.

*In claim 22, column 28, line 29, "X-" should read --X⁻--.

In claim 44, column 29, line 48, "atoms; and wherein" should read --atoms; wherein--.

In claim 44, column 30, delete lines 1-10 in their entirety and insert therefor

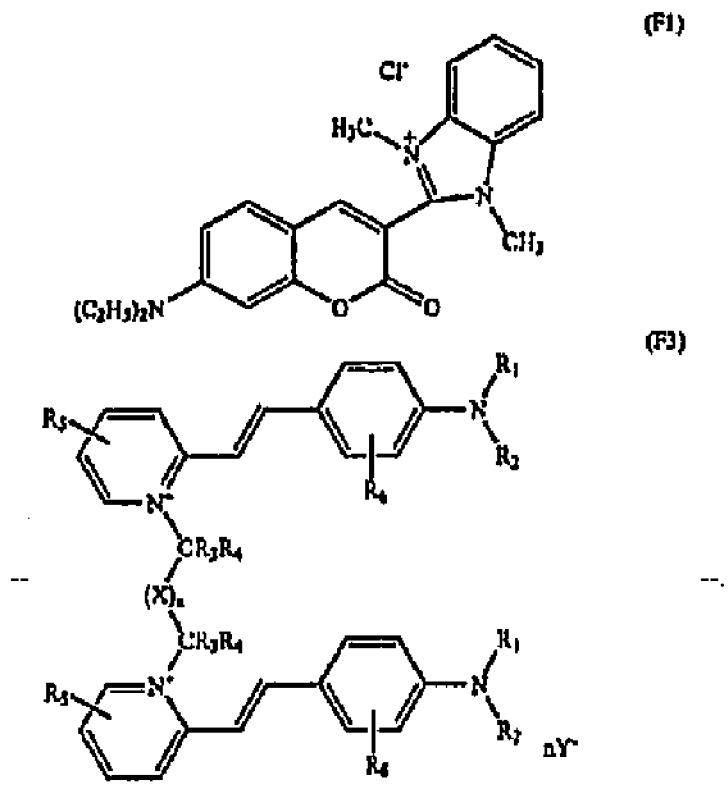

In claim 82, column 33, line 62, "atoms; and further wherein" should read --atoms; wherein--.

In claim 83, column 36, line 17, "atoms; and further wherein" should read --atoms; wherein--.

UNITED STATES PATENT AND TRADEMARK OFFICE
CERTIFICATE OF CORRECTION

PATENT NO. : 7,198,650 B2
APPLICATION NO. : 10/814338
DATED : April 3, 2007
INVENTOR(S) : Chrystel Pourille-Grethen and Grégory Plos It is certified that error appears in the above-identified patent and that said Letters Patent is hereby corrected as shown below:

In claim 85, column 38, line 53, "atoms; and further wherein" should read --atoms; wherein--.

In claim 86, column 40, line 67, "atoms; and further wherein" should read --atoms; wherein--.

Signed and Sealed this

Eleventh Day of September, 2007

JON W. DUDAS
*Director of the United States Patent and Trademark Office*